United States Patent
Chen

(10) Patent No.: US 6,602,274 B1
(45) Date of Patent: Aug. 5, 2003

(54) TARGETED TRANSCUTANEOUS CANCER THERAPY

(75) Inventor: James Chen, Bellevue, WA (US)

(73) Assignee: Light Sciences Corporation, Snoqualmie, WA (US)

( * ) Notice: Subject to any disclaimer, the term of this patent is extended or adjusted under 35 U.S.C. 154(b) by 0 days.

(21) Appl. No.: 09/271,575

(22) Filed: Mar. 18, 1999

Related U.S. Application Data

(60) Provisional application No. 60/116,234, filed on Jan. 15, 1999.

(51) Int. Cl.[7] .......................... A61N 5/06; A61N 5/067; A61N 1/30
(52) U.S. Cl. ............................. 607/88; 607/89; 604/21
(58) Field of Search ............................ 604/21; 607/89, 607/90–92; 606/2–16; 424/178.1, 181.1, 182.1

(56) References Cited

U.S. PATENT DOCUMENTS

| | | | |
|---|---|---|---|
| 4,849,207 A | | 7/1989 | Sakata et al. ................. 424/1.1 |
| 4,932,934 A | * | 6/1990 | Dougherty et al. ............ 604/21 |
| 5,002,962 A | | 3/1991 | Pandey et al. |
| 5,171,749 A | * | 12/1992 | Levy ........................... 514/410 |
| 5,283,255 A | | 2/1994 | Levy et al. .................. 514/410 |
| 5,314,905 A | * | 5/1994 | Pandey et al. ............... 514/410 |
| 5,399,583 A | * | 3/1995 | Levy ........................... 514/410 |
| 5,445,608 A | | 8/1995 | Chen et al. |
| 5,474,765 A | * | 12/1995 | Thorpe ................... 424/178.17 |
| 5,482,698 A | | 1/1996 | Griffiths |
| 5,484,778 A | | 1/1996 | Kenney et al. ................ 514/63 |

(List continued on next page.)

FOREIGN PATENT DOCUMENTS

| | | |
|---|---|---|
| AU | 0674251 | 12/1996 |
| AU | 0694868 | 7/1998 |
| AU | 0708410 | 8/1999 |
| AU | 0713227 | 11/1999 |
| AU | 0720815 | 6/2000 |

(List continued on next page.)

OTHER PUBLICATIONS

Casalini, P. et al., Tumor Pretargeting: Role Of Avidin/Streptavidin On Monoclonal Antibody Internalization, J. Nuclear Med., (1997) 38(9):1378–81.

(List continued on next page.)

*Primary Examiner*—Roy D. Gibson
(74) *Attorney, Agent, or Firm*—Stephanie L. Seidman; Heller Ehrman White & McAuliffe, LLP

(57) ABSTRACT

The present invention is drawn to methods and compounds for photodynamic therapy (PDT) of a target tissue or compositions in a mammalian subject, using a light source that preferably transmits light to a treatment site transcutaneously. The method provides for administering to the subject a therapeutically effective amount of a targeted substance, which is either a targeted photosensitizing agent, or a photosensitizing agent delivery system, or a targeted prodrug. This targeted substance preferably selectively binds to the target tissue. Light at a wavelength or waveband corresponding to that which is absorbed by the targeted substance is then administered. The light intensity is relatively low, but a high total fluence is employed to ensure the activation of the targeted photosensitizing agent or targeted prodrug product. Transcutaneous PDT is useful in the treatment of specifically selected target tissues, such as vascular endothelial tissue, the abnormal vascular walls of tumors, solid tumors of the head and neck, tumors of the gastrointestinal tract, tumors of the liver, tumors of the breast, tumors of the prostate, tumors of the lung, nonsolid tumors, malignant cells of the hematopoietic and lymphoid tissue and other lesions in the vascular system or bone marrow, and tissue or cells related to autoimmune and inflammatory disease.

37 Claims, 6 Drawing Sheets

U.S. PATENT DOCUMENTS

| | | | |
|---|---|---|---|
| 5,484,803 A | 1/1996 | Richter | 514/410 |
| 5,514,669 A | 5/1996 | Selman | 514/63 |
| 5,571,152 A | 11/1996 | Chen et al. | 607/92 |
| 5,630,996 A | 5/1997 | Reno et al. | |
| 5,643,334 A * | 7/1997 | Eckhouse et al. | 606/13 |
| 5,702,432 A | 12/1997 | Chen et al. | |
| 5,705,518 A | 1/1998 | Richter et al. | |
| 5,715,837 A | 2/1998 | Chen | 128/899 |
| 5,736,563 A | 4/1998 | Richter | |
| 5,741,316 A | 4/1998 | Chen et al. | 607/61 |
| 5,766,234 A | 6/1998 | Chen et al. | |
| 5,770,730 A | 6/1998 | Pandey et al. | 540/472 |
| 5,775,339 A * | 7/1998 | Woodburn et al. | 128/898 |
| 5,782,896 A | 7/1998 | Chen et al. | |
| 5,800,478 A | 9/1998 | Chen et al. | |
| 5,807,881 A | 9/1998 | Leong et al. | 514/410 |
| 5,814,008 A | 9/1998 | Chen et al. | 604/21 |
| 5,817,048 A | 10/1998 | Lawandy | 604/20 |
| 5,827,186 A | 10/1998 | Chen et al. | |
| 5,829,448 A | 11/1998 | Fisher et al. | |
| 5,864,035 A | 1/1999 | Pandey et al. | 540/472 |
| 5,865,840 A | 2/1999 | Chen | 607/92 |
| 5,876,427 A | 3/1999 | Chen et al. | 607/88 |
| 5,882,328 A | 3/1999 | Levy et al. | 604/20 |
| 5,913,884 A * | 6/1999 | Trauner et al. | 607/88 |
| 5,921,244 A | 7/1999 | Chen et al. | 128/897 |
| 5,942,534 A | 8/1999 | Trauner et al. | 514/410 |
| 5,945,762 A | 8/1999 | Chen et al. | 310/171 |
| 5,957,960 A | 9/1999 | Chen et al. | 607/92 |
| 5,997,569 A | 12/1999 | Chen et al. | 607/88 |
| 5,997,842 A | 12/1999 | Chen | 424/1.29 |
| 6,015,897 A * | 1/2000 | Theodore et al. | 540/474 |
| 6,058,937 A * | 5/2000 | Doiron et al. | 128/898 |
| 6,080,160 A | 6/2000 | Chen et al. | 606/72 |
| 6,083,485 A | 7/2000 | Licha et al. | 424/9.6 |
| 6,092,531 A | 7/2000 | Chen et al. | 128/899 |
| 6,096,066 A | 8/2000 | Chen et al. | 607/88 |
| 6,100,290 A | 8/2000 | Levy et al. | 514/410 |
| 6,107,325 A | 8/2000 | Chen et al. | 514/410 |
| 6,138,681 A | 10/2000 | Chen et al. | 128/899 |
| 6,210,425 B1 | 4/2001 | Chen | 607/88 |
| 6,217,869 B1 * | 4/2001 | Meyer et al. | 424/178.1 |
| 6,238,426 B1 | 5/2001 | Chen | 607/88 |
| 6,273,904 B1 | 8/2001 | Chen et al. | 607/88 |
| 6,297,228 B1 | 10/2001 | Clark et al. | 514/177 |
| 6,319,273 B1 | 11/2001 | Chen et al. | 607/88 |
| 6,331,744 B1 | 12/2001 | Chen et al. | 310/171 |
| 6,344,050 B1 | 2/2002 | Chen | 607/88 |
| 2001/0046983 A1 | 11/2001 | Pandey et al. | 514/185 |
| 2001/0049502 A1 | 12/2001 | Chen | 604/167.06 |
| 2002/0010500 A1 | 1/2002 | Chen | 607/89 |
| 2002/0049247 A1 | 4/2002 | Chen | 514/410 |
| 2002/0087205 A1 | 7/2002 | Chen | 607/88 |

FOREIGN PATENT DOCUMENTS

| | | |
|---|---|---|
| AU | 0721857 | 7/2000 |
| EP | 0 175 617 | 3/1986 |
| JP | 51-159879 | 7/1978 |
| JP | 57-185220 | 11/1982 |
| WO | WO 93/00005 | 1/1993 |
| WO | 9311657 | 6/1993 |
| WO | WO 93/24127 | 12/1993 |
| WO | WO 94/06424 | 3/1994 |
| WO | WO 95/32001 | 11/1995 |
| WO | 9732520 | 9/1997 |
| WO | WO 97/40679 | 11/1997 |
| WO | 9806456 | 2/1998 |
| WO | 9808565 | 3/1998 |
| WO | 9814243 | 4/1998 |
| WO | 9824371 | 6/1998 |
| WO | 96824510 | 6/1998 |
| WO | 9832491 | 7/1998 |
| WO | 9832492 | 7/1998 |
| WO | 9832493 | 7/1998 |
| WO | 9846130 | 10/1998 |
| WO | 9850034 | 11/1998 |
| WO | WO 98/52610 | 11/1998 |
| WO | 9856302 | 12/1998 |
| WO | 9903503 | 1/1999 |
| WO | 9918879 | 4/1999 |
| WO | 9920346 | 4/1999 |
| WO | 9939769 | 8/1999 |
| WO | 9958149 | 11/1999 |
| WO | 9952565 | 12/1999 |
| WO | 9966988 | 12/1999 |
| WO | 0015296 | 3/2000 |
| WO | 0036983 | 6/2000 |
| WO | 0041725 | 7/2000 |
| WO | 0041726 | 7/2000 |
| WO | 0041727 | 7/2000 |
| WO | 0041768 | 7/2000 |
| WO | 0103770 | 1/2001 |
| WO | 0105316 | 1/2001 |
| WO | 0115694 | 3/2001 |
| WO | 0143825 | 6/2001 |
| WO | 0151087 | 7/2001 |

OTHER PUBLICATIONS

Chen, J., Next Generation Light Delivery System For Multi–Treatment Extended Duration Photodynamic Therapy (MED–PDT), SPIE—Proceeding Series, (1997) 2972:161–167.

Fisher, W.G. et al., Simultaneous Two–Photon Activation Of Type–I Photodynamic Therapy Agents, Photochemistry and Photobiology (1997) 66(2):141–155.

Kreimer–Birnbaum, M., Modified Porphyrins, Chlorins, Phthalocyanines, and Purpurins: Second–Generation Photosensitizers for Photodynamic Therapy, Seminars in Hematology (1989) 26(2):157–73.

Millson, C.E. et al., Ex–Vivo Treatment Of Gastric Helicobacter Infection By Photodynamic Therapy, J. of Photochemistry and Photobiology B:Biology (1996) 32:59–65.

Ruebner, A. et al., Carrier Systems In PDT II: Accumulation Strategies Of Biotin–Avidin Coupled Photosensitizers Developed On Cultured Tumor Cells, SPIE, (1996) 2625:328–32.

Savitsky, A. P. et al., Avidin–Biotin System For Targeting Delivery Of Photosensitizers And Other Cytotoxic Agents Into Malignant Tissues, SPIE, (1997) 3191:343–53.

Sigdestad, C. P. et al., Chemical Modification Of Normal Tissue Damage Induced By Photodynamic Therapy, British J. of Cancer, (1996) 74(Suppl. 37):S89–S92.

Umemura, S. et al., Recent Advances In Sonodynamic Approach To Cancer Therapy, Ultrasonics Sonochemistry, (1996) 3:S187–S191.

Yumita et al., Sonodynamically Induced Antitumor Effect Of Gallium–Porphyrin Complex By Focused Ultrasound On Experimental Kidney Tumor, Cancer Letters, (1997) 112:79–86.

Haas et al., "Phototherapy of Bladder Cancer: Dose/Effect Relationships", Journal of Urology, 136:525–528 (1986).

Parrish, J.A. "Photobiologic Consideration in Photoradiation Therapy," *Porphyrin Photosensitization*, Plenum Press, 91–108 (1983).

Book: Photodynamic Therapy, Basic Principles and Clinical Applications, Henderson, Barbara W. and Dougherty, Thomas J., (Eds.); Marcel Dekker, Inc., New York; Article: Barr et al., "Normal Tissue Damage Following Photodynamic Therapy: Are There Biological Advantages?", pp. 201–216.

Gilson et al., "Therapeutic ratio of photodynamic therapy in the treatment of superficial tumours of skin and subcutaneous tissues in man", *J. Cancer,* 58:665–667 (1988).

Lin et al., "Skin Necrosis due to Photodynamic Action of Benzoporphyrin Depends on Circulating Rather than Tissue Drug Levels: Implications for Control of Photodynamic Therapy", *Photochem. Photobiol.,* 68(4):575–583 (1998).

Mew et al., "Ability of Specific Monoclonal Antibodies and Conventional Antisera Conjugated to Hematoporphyrin to Label and Kill Selected Cell Lines Subsequent to Light Activation", *Cancer Res.,* 45:4380–4386 (1985).

Tomio et al., "Effect of Hematoporphyrin and Red Light on AH–130 Solid Tumors in Rats", *ACTA Radiologica Oncol.,* 22:49–53 (1983).

Yumita et al., "The Combination Treatment of Ultrasound and Antitumor Drugs on Yoshida Sarcoma", *Japan J. Hyperthermic Oncol.,* 3(2):175–182 (1987).

Dillon et al., (1988) "In vitro and in vivo protection against phototoxic side effects of photodynamic therapy by radioprotective agents WR–2721 and WR–77913" *Photochemistry and Photobiology* 48(2):235–238.

Mew et al., (1983) "Photoimmunotherapy: treatment of animal tumors with tumor–specific monoclonal antibody–hematoporphyrin conjugates" *J. of Immunol.* 130)3): 1473–1477.

Nakatani, Y. et al., (1981) "Chemistry and biochemistry of Chinese drugs. VII. Cytostatic pheophytins from silkworm excreta, and derived photocytotoxic pheophorbides" *Chem. Pharm. Bull.* 29(8):2261–2269.

North et al., (1992) "Viral inactivation in blood and red cell concentrates with benzoporphyrin derivative" *Blood Cells* 18:129–140.

Weiman, T.J. (1999) "Photodynamic Therapy (PDT) of locally recurrent breat cancer (LRBC) with lutetium texaphyrin (Lutrin): a phase IB/IIA trial" *Program/Proceedings of American Society of Clinical Oncology,* 35th Annual Meeting, Atlanta, Georgia, vol. 18, p. 111a, Abstract No. 418.

Wilder–Smith et al., (1999) "Photoeradication of *Helicobacter pylori* in humans: phase I study" *AGA Abstracts: Gastroenterology* 116(4):A354, Abstract No. G1546.

Yamamoto, T. (Dec. 10, 1974) "Effect of phytochlorin on transplantable cancer cells" *Medicine and Biology* 89(6):433–438, English translation and certificate of translation included, 7 pages.

Yamamoto, T. (Apr. 10, 1975) "Suppression of tumors by the photodynamic action of phytochlorin sodium" *Medicine and Biology* 90(4):161–164, English translation and certificate of translation.

Yamamoto, T. and Miyagawa, F. (Jun. 10, 1975) "Photodynamic effects on the nucleic acids of cancer cells sensitized by sodium phytochlorin" *Medicine and Biology* 90(6): 397–400, English translation and certificate of translation included, 4 pages.

Yamamoto, T. and Miyagawa, F. (1978) "Photoradiation therapy, phytochlorin and visible light" *Prevention and Detection of Cancer, Part 1, Prevention. Volume 2, Etiology–Prevention Methods* Proceedings of the Third International Symposium on Detection and Prevention of Cancer held Apr. 26, 1976 in New York, NY, 1(2):1789–1802.

Yumita et al., (1987) "Sonodynamically induced antitumor effect of gallium–porphyrin complex by focused ultrasound on experimental kidney tumor" *Japan J. Hyperthermic Oncology* 3(2):175–182.

Adili, Farzin et al., "Local delivery of photosensitizing drugs in arteries: a novel approach to photodynamic therapy for the prevention of intimal hyperplasia", *Proc. SPIE–INT. Soc. Opt. Eng.,* 2395:402–8 (1995) (Ger. Symp. Laser Angioplasty, 2nd, 1980).

Ciulla et al., "Changing therapeutic paradigms for exudative age–relted macular degeneration: antiangiogenic agents and photodynamic therapy", *Exp. Opin. Invest. Drugs,* 8(12):2173–2182 (1999).

Dartsch, et al., "Photodynamic therapy of vascular stenoses? Response of cultured human smooth muscle cells from non–atherosclerotic arteries and atheromatous plaques following treatment with photosensitizing porphyrins", *Proc. SPIE–INT. Soc. Opt. Eng.,* 1462:77–80 (1990).

Dimitroff et al., "Anti–angiogenic activity of selected receptor tyrosine kinase inhibitors, PD166285 and PD173074: Implications for combination treatment with photodynamic therapy" *Investigational New Drugs,* 17:121–135 (1999).

Ferrario et al., "Antiangiogenic Treatment Enhances Photodynamic Therapy Responsiveness in a Mouse Mammary Carcinoma", *Cancer Research,* 60:4066–4069 (2000).

Fisher, W.G. et al., "Simultaneous Two–Photon Activation of Type–1 Photodynamic Therapy Agents," *Photochem. Photobiol.,* 66(2):141–155 (1997).

McMillan et al., "Tumor growth inhition and regression induced by photothermal vascular targeting and angiogenesis inhibitor retinoic acid", *Cancer Lett.,* 137:35–44 (1999).

Renno et al., "Photodynamic Therapy Using Lu–Tex Apoptosis In Vitro, and Its Effect is Potentiated by Angiostatin in Retinal Capillary Endothelial Cells", *Investigative Ophthalmol. & Visual Sci.,* 41(12):3963–3971 (2000).

Ruebner, A. et al. "Carrier Systems in PDT II: Accumulation Strategies of Biotin–Avidin Coupled Photosensitizers Developed On Cultured Tumor Cells," *SPIE,* 2625:328–32 (1996).

Savitsky, A.P. et al. "Avidin–Biotin System for Targeting Delivery of Photosensitizers and Other Cytotoxic Agents Into Malignant Tissues," *SPIE,* 3191: 243–53 (1997).

Sigsestad, C.P. et al. "Chemical Modification of Normal Tissue Damage Induced by Photodynamic Therapy," *Brit. J. Cancer* 74(Suppl.37):S89–92 (1996).

\* cited by examiner

TARGETED TRANSCUTANEOUS CANCER THERAPY

RELATED APPLICATIONS

Benefit of priority under 35 U.S.C. §119(e) to the following provisional application is claimed herein: U.S. provisional application Ser. No. 60/116,234 to James Chen, filed Jan. 15, 1999, entitled "TARGETED TRANSCUTANEOUS CANCER THERAPY". This application is incorporated by reference in its entirety.

FIELD OF THE INVENTION

This invention generally relates to the delivery to a tumor target site of a therapeutically effective amount of a photosensitizing agent that is activated by a relatively low fluence rate or level of intensity of light administered over a prolonged period of time, and more specifically, to the delivery of a photosensitizing agent that is targeted to bind with cancerous cells at the target site.

BACKGROUND OF THE INVENTION

One form of energy activated therapy for destroying abnormal or diseased tissue is photodynamic therapy (PDT). PDT is a two-step treatment process, which has received increasing interest as a mode of treatment for a wide variety of different cancers and diseased tissue. The first step in this therapy is carried out by administering a photosensitive compound systemically by ingestion or injection, or topically applying the compound to a specific treatment site on a patient's body, followed by illumination of the treatment site with light having a wavelength or waveband corresponding to a characteristic absorption waveband of the photosensitizer. The light activates the photosensitizing compound, causing singlet oxygen radicals and other reactive species to be generated, leading to a number of biological effects that destroy the abnormal or diseased tissue, which has absorbed the photosensitizing compound. The depth and volume of the cytotoxic effect on the abnormal tissue, such as a cancerous tumor, depend in part on the depth of the light penetration into the tissue, the photosensitizer concentration and its cellular distribution, and the availability of molecular oxygen, which will depend upon the vasculature system supplying the abnormal tissue or tumor.

Various types of PDT light sources and their methods of use have been described in the prior art literature. However, publications describing appropriate light sources and the effects of transcutaneous light delivery to internal treatment sites within a patient's body, for PDT purposes, are relatively limited in number. It has generally been accepted that the ability of a light source external to the body to cause clinically useful cytotoxicity during PDT is limited in depth to a range of 1–2 cm or less, depending on the photosensitizer.

Treatment of superficial tumors in this manner has been associated with inadvertent skin damage due to accumulation of the photosensitizer in normal skin tissue, which is a property of all systemically administered photosensitizers in clinical use. For example, clinically useful porphyrins such as PHOTOPHRIN™ (a QLT, Ltd. brand of sodium porfimer) are associated with general dermal photosensitivity lasting up to six weeks. PURLYTIN™, which is a brand of purpurin, and FOSCAN™, which is brand of chlorin, sensitize the skin to light for at least several weeks, so that patients to whom these drugs are administered must avoid exposure to sunlight or other bright light sources during this time to avoid unintended phototoxic effects on the normal dermal tissue. Indeed, efforts have been made to develop photoprotectants to reduce skin photosensitivity (see, for example: Dillon et al., "Photochemistry and Photobiology," 48(2): 235–238 (1988); and Sigdestad et al., British J. of Cancer, 74:S89–S92, (1996)).

Recently, it has been reported that a relatively intense external laser light source might be employed transcutaneously to cause two-photon absorption by a photosensitizer at a greater depth within a patient's body, so that it is theoretically possible to cause a very limited volume of cytotoxicity in diseased tissue at greater depths than previously believed possible. However, no clinical studies exist to support this contention. One would expect that the passage of an intense beam of light through the skin would lead to the same risk of phototoxic injury to non-target normal tissues, such as skin and subcutaneous normal tissue, if this light is applied in conjunction with a systemically administered photosensitizer.

For example, one PDT modality discloses the use of an intense laser source to activate a photosensitizer drug within a precisely defined boundary (see: U.S. Pat. No. 5,829,448, Fisher et al., "Method for improved selectivity in photoactivation of molecular agents"). The two-photon methodology requires a high power, high intensity laser for drug activation using a highly collimated beam, with a high degree of spatial control. For a large tumor, this treatment is not practical, since the beam would have to be swept across the skin surface in some sort of set, repeating pattern, so that the beam encompasses the entire volume of the tumor. Patient or organ movement would be a problem, because the beam could become misaligned. Exposure of normal tissue or skin in the path of the beam and subcutaneous tissue photosensitivity is not addressed in the prior art literature. Any photosensitizer absorbed by normal tissue in the path of the beam will likely be activated and cause unwanted collateral normal tissue damage. Clearly, it would be preferable to employ a technique that minimizes the risk of damage to normal tissue and which does not depend upon a high intensity laser light source to produce two photon effects. Further, it would be preferable to provide a prolonged exposure of an internal treatment site with light at a lower fluence rate or lower intensity, which tends to reduce the risk of harm to non-target tissue or skin and subcutaneous normal tissue and reduces any collateral tissue damage due to phototoxicity.

Other PDT modalities have employed the use of a light source producing a low total fluence delivered over a short time period to avoid harm to skin caused by activation of a photosensitizer and have timed the administration of such drugs to better facilitate destruction of small tumors in animals (see, for example, U.S. Pat. No. 5,705,518, Richter et al.). However, although not taught or suggested by the prior art, it would be preferable to employ a light source that enables a relatively large total fluence PDT, but at a lower intensity so that larger tumor volumes can more readily be treated.

If, as is often the case, a target tumor tissue lies below an intact cutaneous layer of normal tissue, the main drawbacks of all transcutaneous illumination methods, whether they be external laser or external non-laser light sources, are: (1) the risk of damage to non-target tissues, such as the more superficial cutaneous and subcutaneous tissues overlying the target tumor mass; (2) the limited volume of a tumor that can be treated; and (3) the limitation of treatment depth. Damage to normal tissue lying between the light source and the target tissue in a tumor occurs due to the uptake of photosensitizer by the skin and other tissues overlying the tumor mass, and the resulting undesired photoactivation of the photosensitizer absorbed by these tissues. The consequences of inadvertent skin damage caused by transcutaneous light delivery to a subcutaneous tumor may include severe pain, serious infection, and fistula formation. The limited volume of tumor that can be clinically treated and the limitations of the light penetration below the skin surface in turn have led those skilled in this art to conclude that clinical transcutaneous PDT is only suitable for treatment of superficial, thin lesions.

U.S. Pat. No. 5,445,608, Chen et al., discloses the use of implanted light sources for internally administering PDT. Typically, the treatment of any internal cancerous lesions with PDT requires at least a minimally invasive procedure such as an endoscopic technique, for positioning the light source proximate to the tumor, or open surgery to expose the tumor site. There is some risk associated with any internal procedure performed on the body. Clearly, there would be significant advantage to a completely noninvasive form of PDT directed to subcutaneous and deep tumors, which avoids the inadvertent activation of any photosensitizer in skin and intervening tissues. To date, this capability has not been clinically demonstrated nor realized. Only in animal studies utilizing mice or other rodents with very thin cutaneous tissue layers, have very small superficial subcutaneous tumors been treated with transcutaneously transmitted light. These minimal in vivo studies do not provide an enabling disclosure or even suggest how transcutaneous light sources might safely be used to treat large tumors in humans with PDT, however.

Another PDT modality in the prior art teaches the destruction of abnormal cells that are circulating in the blood using light therapy, while leaving the blood vessels intact (see, for example: U.S. Pat. No. 5,736,563, Richter et al.; WO 94/06424, Richter; WO 93/00005, Champan et al.; U.S. Pat. No. 5,484,803, Richter et al., and WO 93/24127, North et al. Instead, it might be preferable to deliberately damage and occlude blood vessels that form the vasculature supplying nutrients and oxygen to a tumor mass, thus rendering a given volume of abnormal tissue in the tumor (not circulating cells) ischemic and anoxic and thus promoting the death of the tumor tissue serviced by these blood vessels.

To facilitate the selective destruction of the blood vessels that service a tumor, it would be desirable to selectively bind a photosensitizing agent to specific target tissue antigens, such as those found on the epithelial cells comprising tumor blood vessels. This targeting scheme should decrease the amount of photosensitizing drug required for effective PDT, which in turn should reduce the total light energy, and the light intensity needed for effective photoactivation of the drug. Even if only a portion of a blood vessel is occluded as a result of the PDT, downstream thrombosis is likely to occur, leading to a much greater volume of tumor necrosis compared to a direct cytotoxic method of destroying the tumor cells, in which the photosensitizer drug must be delivered to all abnormal cells that are to be destroyed. One method of ensuring highly specific uptake of a photosensitizer by epithelial cells in tumor vessels would be to use the avidin-biotin targeting system. Highly specific binding of a targeted agent such as a PDT drug to tumor blood vessels (but not to the cells in normal blood vessels) is enabled by this two step system. While there are reports in the scientific literature describing the binding between biotin and streptavidin to target tumor cells, there are no reports of using this ligand-receptor binding pair to bind with cells in tumor vessels nor in conjunction with carrying out prolonged PDT light exposure (see, for example: Savitsky et al., SPIE, 3191:343–353, (1997); and Ruebner et al., SPIE, 2625:328–332, (1996)). In a non-PDT modality, the biotin-streptavidin ligand-receptor binding pair has also been reported as useful in binding tumor targeting conjugates with radionuclides (see U.S. Pat. No. 5,630,996, Reno et al.) and with monoclonal antibodies (see Casalini et al.; *J. Nuclear Med.*, 38(9):1378–1381, (1997)) and U.S. Pat. No. 5,482,698, Griffiths).

Other ligand-receptor binding pairs have been used in PDT for targeting tumor antigens, but the prior art fails to teach their use in conjunction with targeting cells in blood vessels or treatment of large, established tumors (see, for example, Mew et al., *J. of Immunol.*, 130(3): 1473–1477, (1983)).

High powered lasers are usually employed as a light source in administering PDT to shorten the time required for the treatment (see W. G. Fisher, et al., *Photochemistry and Photobiology*, 66(2):141–155, (1997)). However, it would likely be safer to use a low power, non-coherent light source that remains energized for two or more hours to increase the depth of the photoactivation. This approach is contrary to the prior art that recommends PDT be carried out with a brief exposure from a high powered, collimated light source.

Recently, there has been much interest in the use of antiangiogenesis drugs for treating cancerous tumors by minimizing the blood supply that feeds a tumor's growth. However, targeting of tumor vessels using antiangiogenesis drugs may lead to reduction in size of small tumors and may prevent new tumor growth, but will likely be ineffective in causing reliable regression of large, established tumors in humans. However, by using a combination of antiangiogenesis and a photosensitizer in the targeting conjugate, it is likely that a large volume tumor can be destroyed by administering PDT.

In treating large tumors, a staged procedure may be preferable in order to control tumor swelling and the amount of necrotic tissue produced as the PDT causes destruction of the tumor mass. For example, by activating a photosensitizer bound to tumor vessels in the center of a large tumor and then sequentially expanding the treatment zone outward in a stepwise manner, a large volume tumor can be gradually ablated in a controlled fashion in order to prevent swelling due to edema and inflammation, which is problematic in organs such as the brain.

Delivered in vivo, PDT has been demonstrated to cause vessel thrombosis and vascular constriction, occlusion, and collapse. And though the treatment of very superficial, thin tumors has been reported using transcutaneous light, there are no clinical reports of transcutaneous light activation being used to destroy deeper, thick tumors that are disposed more than 2 cm below the skin surface. Clearly, there is a need for a PDT paradigm that enables large volume tumors that are disposed well below the surface of the skin to be destroyed with transcutaneous light activation.

It is apparent that the usual method of administering PDT to treat bulky tumors, which relies on invasive introduction of optical fibers, is not the best approach. It would be highly advantageous to apply light transcutaneously in a completely noninvasive method to treat such large tumors (as well as small and even microscopic tumors), without risking damage to non-target tissues, such as skin and normal subcutaneous tissue. Instead of the conventional technique, a method of photoactivation and a series of photosensitizer constructs is needed that enable PDT-induced cytotoxicity, on both a macro and microscopic scale, without risk to the cutaneous layer, or any surrounding normal tissues. Also, the therapeutic index should be enhanced if a specific photosensitizer drug targeting scheme is employed.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this specification are hereby incorporated by reference herein, in their entirety.

SUMMARY OF THE INVENTION

In accord with the present invention, a method is defined for transcutaneously administering a photodynamic therapy to a target tissue in a mammalian subject. The method includes the step of administering to the subject a therapeutically effective amount of either a photosensitizing agent having a characteristic light absorption waveband, a photosensitizing agent delivery system that delivers the photosensitizing agent, or a prodrug that produces a prodrug product having a characteristic light absorption waveband. The photosensitizing agent, photosensitizing agent delivery system, or prodrug selectively binds to the target tissue. Light having a waveband corresponding at least in part with the characteristic light absorption waveband of said photosensitizing agent or of the prodrug is used for transcutaneously irradiating at least a portion of the mammalian subject. An intensity of the light used for irradiating is substantially less than 500 mw/cm$^2$, and a total fluence of the light is sufficiently high to activate the photosensitizing agent or the prodrug product, as applicable.

Preferably, sufficient time is allowed for any of the photosensitizing agent, the photosensitizing agent delivery system, or the prodrug (depending upon which one of these was administered) that is not bound to the target tissue to clear from non-target tissues of the mammalian subject prior to the step of irradiating with the light.

In one application of the invention, the target tissue is vascular endothelial tissue. In another application, the target tissue is an abnormal vascular wall of a tumor. As further defined, the target tissue is selected from the group consisting of: a vascular endothelial tissue, an abnormal vascular wall of a tumor, a solid tumor, a tumor of a head, a tumor of a neck, a tumor of a gastrointestinal tract, a tumor of a liver, a tumor of a breast, a tumor of a prostate, a tumor of a lung, a nonsolid tumor, malignant cells of one of a hematopoietic tissue and a lymphoid tissue, lesions in a vascular system, a diseased bone marrow, and diseased cells in which the disease is one of an autoimmune and an inflammatory disease. In yet a further application of the present invention, the target tissue is a lesion in a vascular system. It is contemplated that the target tissue is a lesion of a type selected from the group consisting of atherosclerotic lesions, arteriovenous malformations, aneurysms, and venous lesions.

The step of irradiating generally comprises the step of providing a light source that is activated to produce the light. In one preferred embodiment of the invention, the light source is disposed external to an intact skin layer of the mammalian subject during the step of irradiating. In another preferred embodiment, the method includes the step of inserting the light source underneath an intact skin layer, but external to an intact surface of an organ of the mammalian subject, and the organ comprises the target tissue.

Preferably, the photosensitizing agent is conjugated to a ligand. The ligand may be either an antibody or an antibody fragment that is specific in binding with the target tissue. Alternatively, the ligand is a peptide, or a polymer, either of which is specific in binding with the target tissue.

The photosensitizing agent is preferably selected from the group consisting of indocyanine green (ICG), methylene blue, toluidine blue, aminolevulinic acid (ALA), chlorins, phthalocyanines, porphyrins, purpurins, texaphyrins, and other photosensitizer agents that have a characteristic light absorption peak in a range of from about 500 nm to about 1100 nm.

The step of irradiating is preferably carried out for a time interval of from about 30 minutes to about 72 hours, or more preferably, from about 60 minutes to about 48 hours, or most preferably, from about 3 hours to about 24 hours.

In yet another application of the invention, the target tissue is bone marrow, or comprises cells afflicted with either an autoimmune disease or an inflammatory disease.

An additional application of the invention contemplates a method for administering photodynamic therapy to a target composition in a mammalian subject by transillumination. The target composition may include one or more pathogenic agents, including: bacteria, viruses, fungi, protozoa, and toxins as well as tissues infected or infiltrated therewith.

Preferably, the total fluence of the light used for irradiating is between about 30 Joules and about 25,000 Joules, more preferably, between about 100 Joules and about 20,000 Joules, and most preferably, between about 500 Joules and about 10,000 Joules.

Another application of the present invention uses an energy activated compound that has a characteristic energy absorption waveband. The energy activated compound selectively binds to the target tissue. Energy having a waveband corresponding at least in part with the characteristic energy absorption waveband of said energy activated compound is used for transcutaneously irradiating at least a portion of the mammalian subject. Preferably the waveband is in the ultrasonic range of energy. Said compound is activated by said irradiating step, wherein the intensity of said ultrasonic energy is substantially less than that level which would result in damage to normal tissue, but at a sufficiently high total fluence of ultrasonic energy that is absorbed by said compound which in turn destroys the target tissue to which it is bound. Preferably, the total fluence of the ultrasonic energy used for irradiating is between about 5 kHz and more than about 300 MHz, more preferably, between about 10 kHz and more than about 200 MHz, and most preferably, between about 20 kHz and more than about 100 MHz.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

Figure 9:
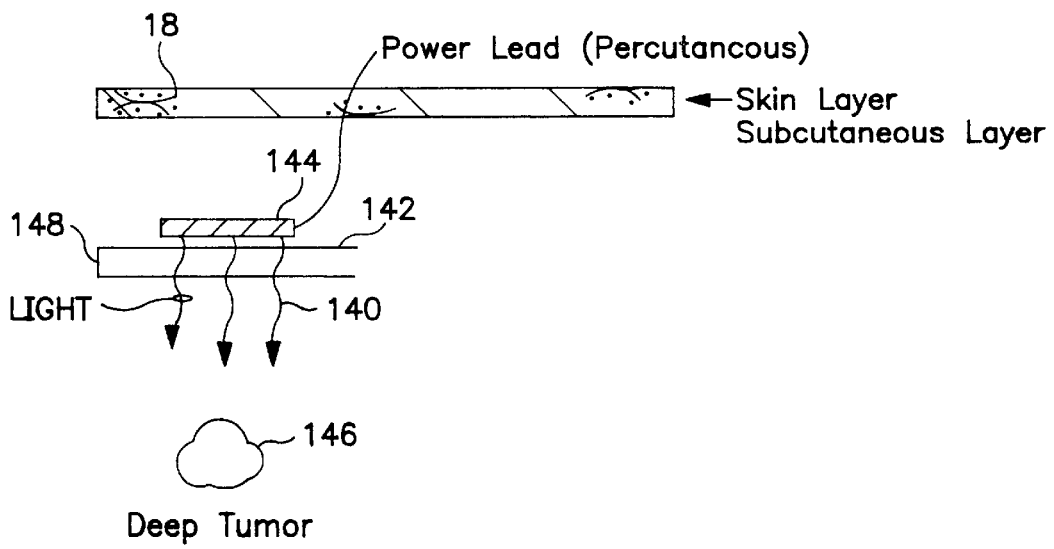
Figure 4A:
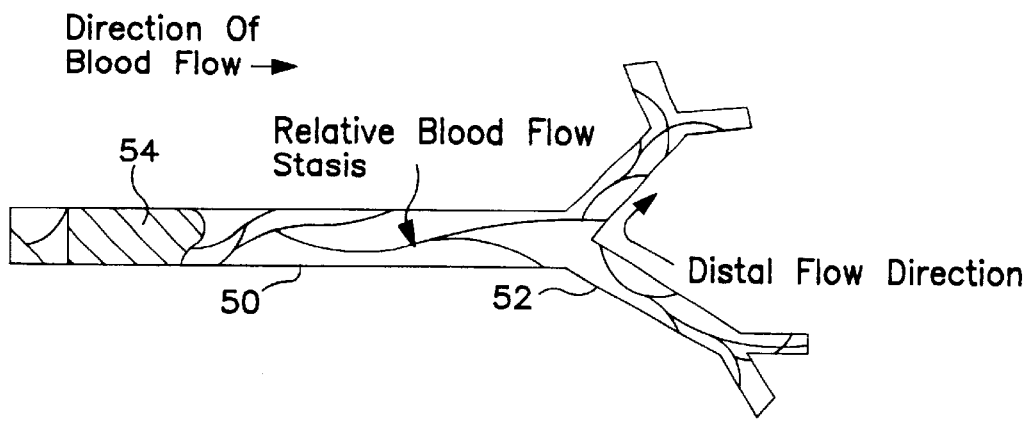
Figure 4B:
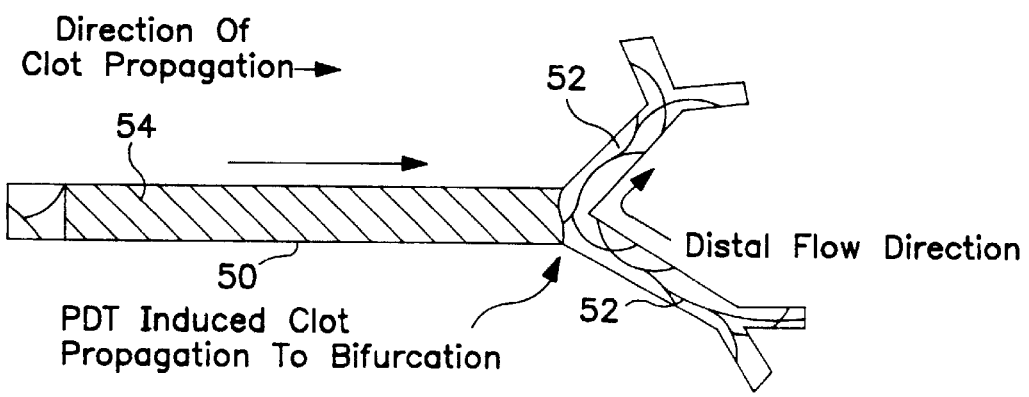
Figure 4C:
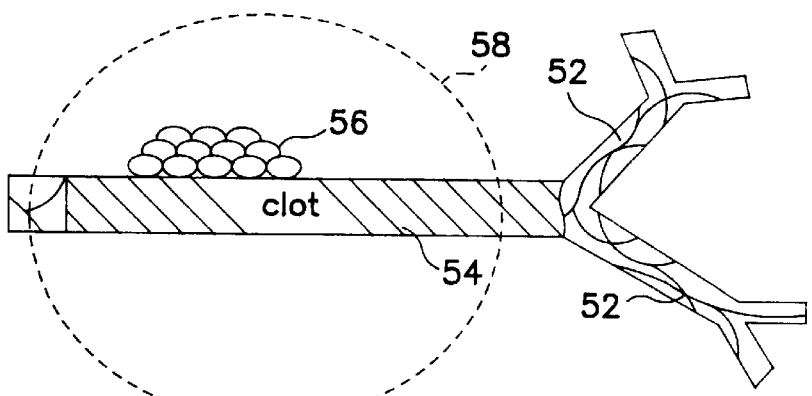
Figure 5:
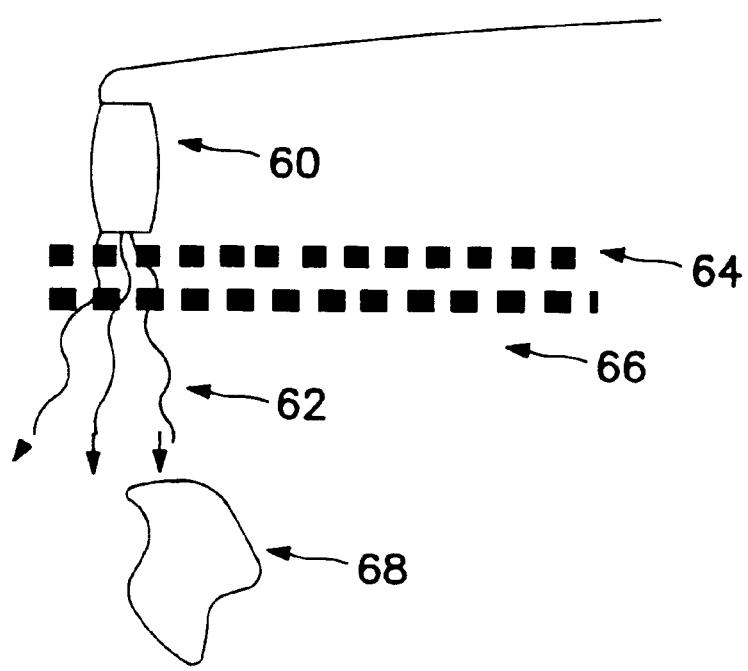
Figure 6:
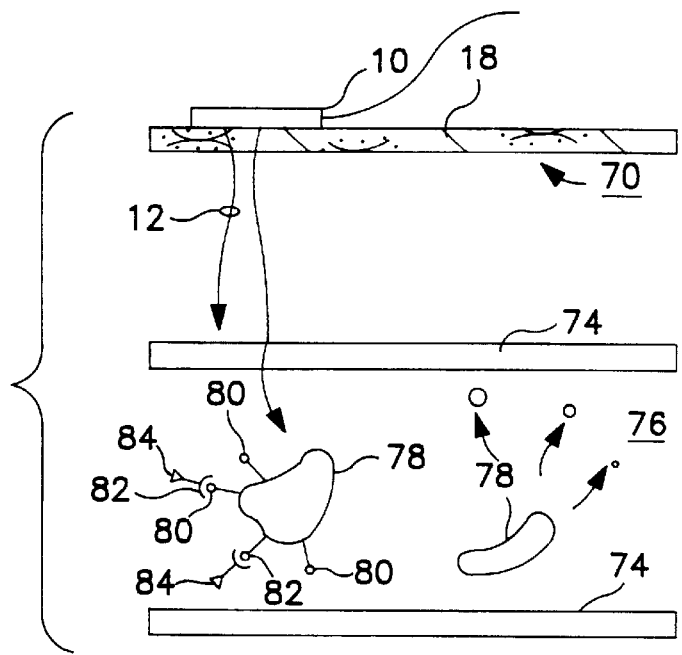
Figure 7:
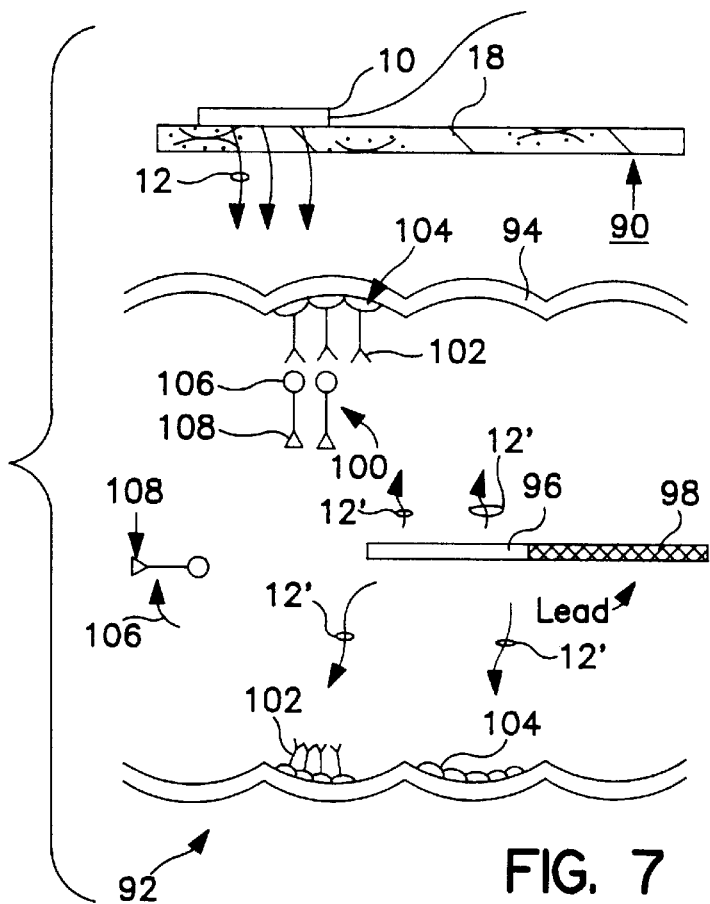
Figure 8:
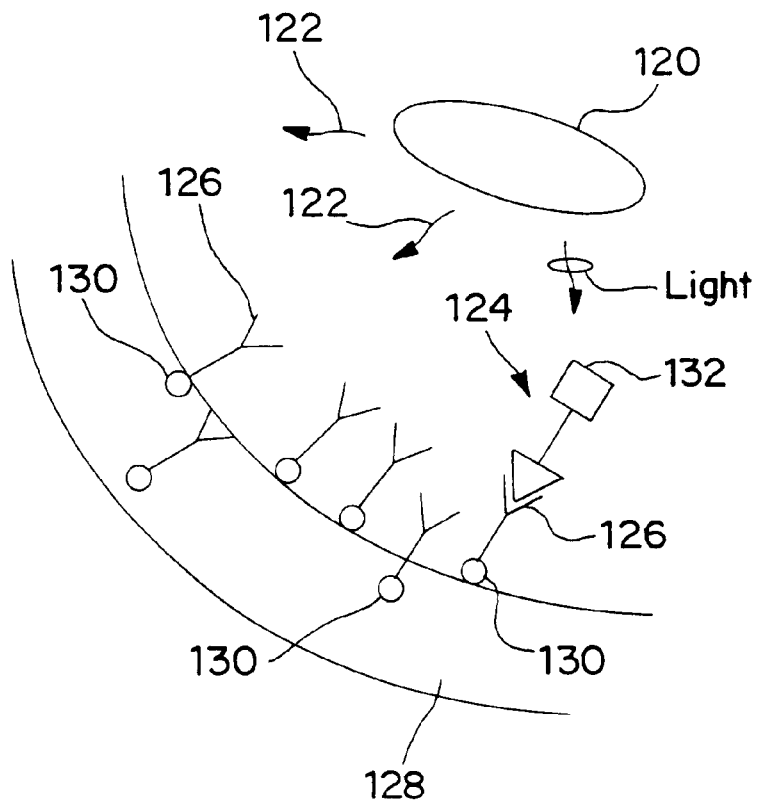

FIGS. 4A–4C schematically illustrate tissue amplified infarction downstream of photodynamic transcutaneous therapy applied to endothelium tissue;

FIG. 5 is a schematic diagram illustrating the use of an external ultrasound source for transcutaneous application of PDT to a deep tumor;

FIG. 6 is a schematic diagram showing the use of an external light source for transcutaneous treatment of intraosseous disease;

FIG. 7 is a schematic diagram showing both an external light source transcutaneously administering light and an intraluminal light source position within either the terminal ileum or colon to treat Crohn's disease with targeted PDT;

FIG. 8 is a schematic diagram illustrating an intraluminal light source in the form of a capsule or pill for administering light to destroy *H. pylori* on the gastric lining with targeted PDT; and FIG. 9 is a schematic diagram showing how an internal light source administers transillumination of a deep tumor through an organ wall to provide targeted PDT that destroys the tumor.

DESCRIPTION OF THE PREFERRED EMBODIMENT

Introduction and General Description of the Invention

This invention is directed to methods and compositions for therapeutically treating a target tissue or destroying or impairing a target cell or a biological component in a mammalian subject by the specific and selective binding of a photosensitizer agent to the target tissue, cell, or biological component. At least a portion of the subject is irradiated with light at a wavelength or waveband within a characteristic absorption waveband of the photosensitizing agent. The light is administered at a relatively low fluence rate or intensity, but at an overall high total fluence dose, resulting in minimal collateral normal tissue damage. It is contemplated that an optimal total fluence for the light administered to a patient will be determined clinically, using a light dose escalation trial. It is further contemplated that the total fluence administered during a treatment will preferably be in the range of 30 Joules to 25,000 Joules, more preferably, in the range from 100 Joules to 20,000 Joules, and most preferably, in the range from 500 Joules to 10,000 Joules.

The terminology used herein is generally intended to have the art recognized meaning and any differences therefrom as used in the present disclosure, will be apparent to the ordinary skilled artisan. For the sake of clarity, terms may also have a particular meaning, as will be clear from their use in context. For example, "transcutaneous" as used in regard to light in this specification and in the claims that follow, more specifically herein refers to the passage of light through unbroken tissue. Where the tissue layer is skin or dermis, transcutaneous includes "transdermal" and it will be understood that the light source is external to the outer skin layer. However, the term "transillumination" as used herein refers to the passage of light through a tissue layer, such as the outer surface layer of an organ, e.g., the liver, and it will be apparent that the light source is external to the organ, but internal or implanted within the subject or patient.

One aspect of the present invention provides for the precise targeting of photosensitive agents or drugs and compounds to specific target antigens of a subject or patient and to the method for activating the targeted photosensitizer agents by subsequently administering to the subject light at a relatively low fluence rate or intensity, over a prolonged period of time, from a light source that is external to the target tissue in order to achieve maximal cytotoxicity of the abnormal tissue, with minimal adverse side effects or collateral normal tissue damage.

Figure 1:
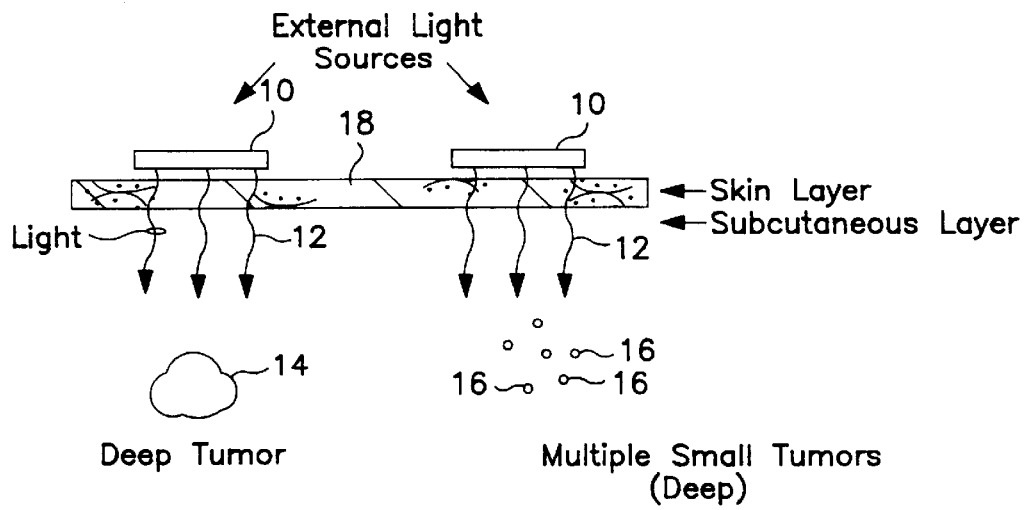
FIG. 1 is a schematic diagram illustrating an external light source being used to administer transcutaneous cancer therapy to a relatively large, singular tumor, and to multiple, small tumors.

FIG. 1 illustrates transcutaneous delivery of light 12 from an external source 10 to a relatively deep tumor 14, or to a plurality of small, but relatively deep tumors 16. The light emitted by external source 10 is preferably of a longer waveband, but still within an absorption waveband of the photosensitive agent (not shown in this Figure) that has been selectively linked to tumor 14 and smaller tumors 16. The longer wavelength of light 12 enables it to pass through a dermal layer 18 and penetrate into the patient's body beyond the depth of tumor(s) being treated with targeted PDT. In these two examples, the PDT is directed specifically at target cells in tumor 14 or in tumors 16.

As used in this specification and the following claims, the terms "target cells" or "target tissues" refer to those cells or tissues, respectively that are intended to be impaired or destroyed by PDT delivered in accord with the present invention. Target cells or target tissues take up or bind with the photosensitizing agent, and, when sufficient light radiation of the waveband corresponding to the characteristic waveband of the photosensitizing agent is applied, these cells or tissues are impaired or destroyed. Target cells are cells in target tissue, and the target tissue includes, but is not limited to, vascular endothelial tissue, abnormal vascular walls of tumors, solid tumors such as (but not limited to) tumors of the head and neck, tumors of the gastrointestinal tract, tumors of the liver, tumors of the breast, tumors of the prostate, tumors of the lung, nonsolid tumors and malignant cells of the hematopoietic and lymphoid tissue, other lesions in the vascular system, bone marrow, and tissue or cells related to autoimmune disease.

Further, target cells include virus-containing cells, and parasite-containing cells. Also included among target cells are cells undergoing substantially more rapid division as compared to non-target cells. The term "target cells" also includes, but is not limited to, microorganisms such as bacteria, viruses, fungi, parasites, and infectious agents. Thus, the term "target cell" is not limited to living cells but also includes infectious organic particles such as viruses. "Target compositions" or "target biological components" include, but are not be limited to: toxins, peptides, polymers, and other compounds that may be selectively and specifically identified as an organic target that is intended to be impaired or destroyed by this treatment method.

Figure 2:
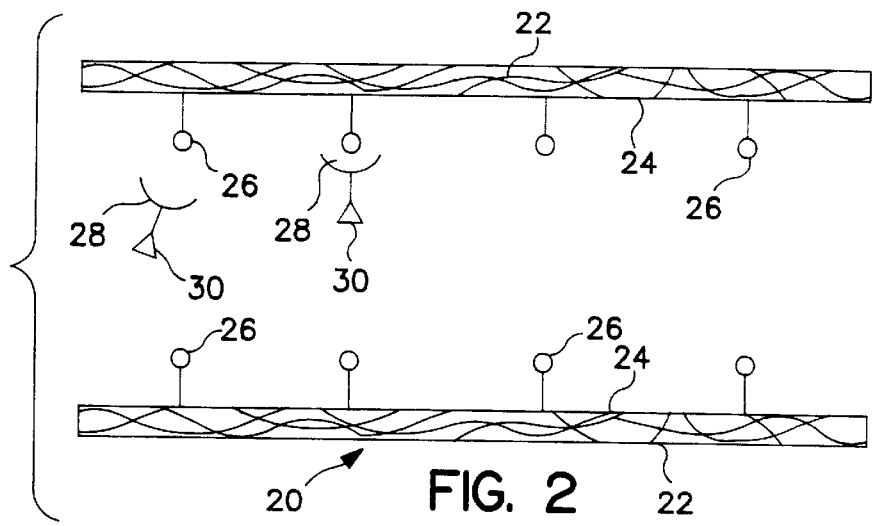
FIG. 2 is a schematic cross-sectional view of a section of a tumor blood vessel, illustrating binding of an antibody/photosensitive drug to endothelial tissue.

FIG. 2 includes a section of a tumor blood vessel 20 having a wall 22, with an endothelial lining 24. A plurality of endothelial antigens 26 are disposed along the endothelial lining. In this example, antibodies 28 that is specific to endothelial antigens 26 have been administered and are shown binding with the endothelial antigens. Coupled to antibodies 28 are PDT photosensitive drug molecules 30. Thus, the PDT photosensitive drug molecules are bound to the endothelial antigens via antibodies 28, but are not bound to non-target cells, since the antibodies are selective only to the endothelial antigens.

"Non-target cells" are all the cells of a mammal that are not intended to be impaired, damaged, or destroyed by the treatment method rendered in accord with the present invention. These non-target cells include but are not limited to healthy blood cells, and other normal tissue, not otherwise identified to be targeted.

"Destroy" means to kill the desired target cell. "Impair" means to change the target cell in such a way as to interfere with its function. For example, in North et al., it is observed that after virus-infected T cells treated with benzoporphyrin derivatives ("BPD") were exposed to light, holes developed in the T cell membrane and increased in size until the membrane completely decomposed (*Blood Cells* 18:129–40, (1992)). Target cells are understood to be impaired or destroyed even if the target cells are ultimately disposed of by macrophages.

"Energy activated agent" is a chemical compound that binds to one or more types of selected target cells and, when exposed to energy of an appropriate waveband, absorbs the energy, causing substances to be produced that impair or destroy the target cells.

"Photosensitizing agent" is a chemical compound that binds to one or more types of selected target cells and, when exposed to light of an appropriate waveband, absorbs the light, causing substances to be produced that impair or destroy the target cells. Virtually any chemical compound that preferentially is absorbed or bound to a selected target and absorbs light causing the desired therapy to be effected may be used in this invention. Preferably, the photosensitizing agent or compound is nontoxic to the animal to which it is administered or is capable of being formulated in a nontoxic composition that can be administered to the animal. In addition, following exposure to light, the photosensitizing agent in any resulting photodegraded form is also preferably nontoxic. A comprehensive listing of photosensitive chemicals may be found in Kreimer-Bimbaum, Sem. Hematol, 26:157–73, (1989). Photosensitive agents or compounds include, but are not limited to, chlorins, bacteriochlorins, phthalocyanines, porphyrins, purpurins, merocyanines, psoralens, benzoporphyrin derivatives (BPD), and porfimer sodium and pro-drugs such as delta-aminolevulinic acid, which can produce photosensitive agents such as protoporphyrin IX. Other suitable photosensitive compounds include ICG, methylene blue, toluidine blue, texaphyrins, and any other agent that absorbs light in a range of 500 nm–1100 nm.

The term "prodrug" is used herein to mean any of a class of substances that are not themselves photosensitive agents, but when introduced into the body, through metabolic, chemical, or physical processes, are converted into a photosensitive agent. In the following disclosure, an aminolevulinic acid (ALA) is the only exemplary prodrug. After being administered to a patient, ALA is metabolically converted into a porphyrin compound that is an effective photosensitive agent.

"Radiation" as used herein includes all wavelengths and wavebands. Preferably, the radiation wavelength or waveband is selected to correspond with or at least overlap the wavelength(s) or wavebands that excite the photosensitive compound. Photosensitive agents or compound typically have one or more absorption wavebands that excite them to produce the substances, which damage or destroy target tissue, target cells, or target compositions. Even more preferably, the radiation wavelength or waveband matches the excitation wavelength or waveband of the photosensitive compound and has low absorption by the non-target cells and the rest of the intact animal, including blood proteins. For example, a preferred wavelength of light for ICG is in the range 750–850 nm.

The radiation used to activate the photosensitive compound is further defined in this invention by its intensity, duration, and timing with respect to dosing a target site. The intensity or fluence rate must be sufficient for the radiation to penetrate skin and reach the target cells, target tissues, or target compositions. The duration or total fluence dose must be sufficient to photoactivate enough photosensitive agent to achieve the desired effect on the target site. Both intensity and duration are preferably limited to avoid over treating the subject or animal. Timing with respect to the dosage of the photosensitive agent employed is important, because (1) the administered photosensitive agent requires some time to home in on target cells, tissue, or compositions at the treatment site, and (2) the blood level of many photosensitive agents decreases with time.

The present invention provides a method for providing a medical therapy to an animal, and the term "animal" includes, but is not limited to, humans and other mammals. The term "mammals" or "mammalian subject" includes farm animals, such as cows, hogs and sheep, as well as pet or sport animals such as horses, dogs, and cats.

Reference herein to "intact animal" means that the whole, undivided animal is available to be exposed to radiation. No part of the animal is removed for exposure to the radiation, in contrast with photophoresis, in which an animal's blood is circulated outside its body for exposure to radiation. However, in the present invention, the entire animal need not be exposed to radiation. Only a portion of the intact animal subject may or need be exposed to radiation, sufficient to ensure that the radiation is administered to the treatment site where the target tissue, cells, or compositions are disposed.

In the present invention, a photosensitizing agent is generally administered to the animal before the animal is subjected to radiation. Preferred photosensitizing agents include, but are not limited to, chlorins, bacteriochlorins, phthalocyanines, porphyrins, purpurins, merocyanines, psoralens and pro-drugs such as .delta.-aminolevulinic acid, which can produce drugs such as protoporphyrin. More preferred photosensitizing agents are: methylene blue, toluidine blue, texaphyrins, and any other agent that absorbs light having a wavelength or waveband in the range from 600 nm–1100 nm. Most preferred of the photosensitizing agents is ICG. The photosensitizing agent is preferably administered locally or systemically, by oral ingestion, or by injection, which may be intravascular, subcutaneous, intramuscular, intraperitoneal or directly into a treatment site, such as intratumoral. The photosensitizing agent also can be administered enterally or topically via patches or implants.

The photosensitizing agent also can be conjugated to specific ligands known to be reactive with a target tissue, cell, or composition, such as receptor-specific ligands or immunoglobulins or immunospecific portions of immunoglobulins, permitting them to be more concentrated in a desired target cell or microorganism than in non-target tissue or cells. The photosensitizing agent may be further conjugated to a ligand-receptor binding pair. Examples of a suitable binding pair include but are not limited to: biotin-streptavidin, chemokine-chemokine receptor, growth factor-growth factor receptor, and antigen-antibody. As used herein, the term "photosensitizing agent delivery system" refers to a photosensitizing agent conjugate, which because of its conjugation, has increased selectivity in binding to a target tissue, target cells, or target composition. The use of a photosensitizing agent delivery system is expected to reduce the required dose level of the conjugated photosensitizing agent, since the conjugate material is more selectively targeted at the desired tissue, cell, or composition, and less of it is wasted by distribution into other tissues whose destruction should be avoided.

Figure 3A:
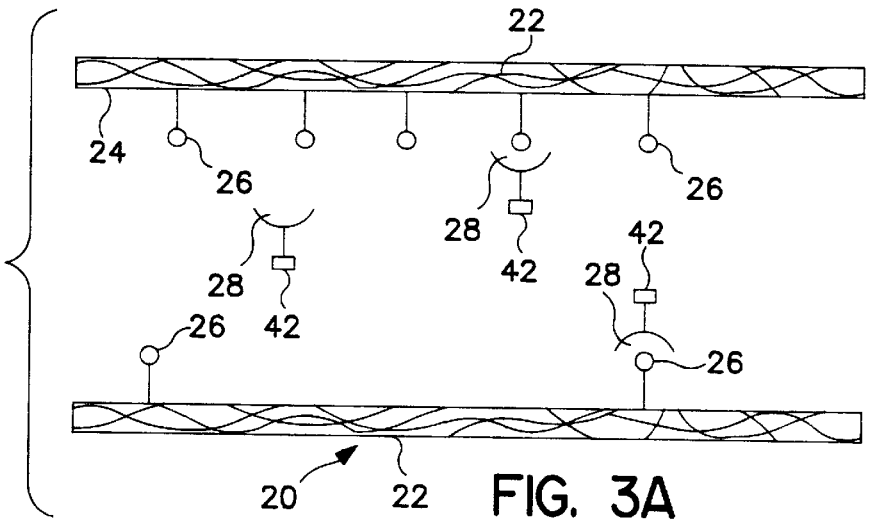
FIGS. 3A and 3B are schematic diagrams illustrating biotin-avidin targeting of endothelial antigens for use in rendering PDT.
Figure 3B:
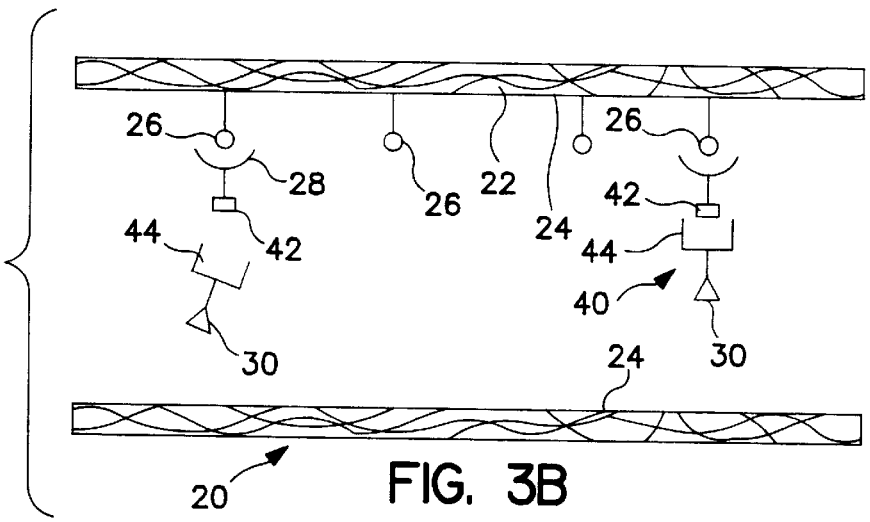

In FIGS. 3A and 3B, an example of a photosensitizing agent delivery system 40 is illustrated in which the target tissue is endothelial layer 24, which is disposed along blood vessel wall 22 of tumor blood vessel 20. As shown in FIG. 3A, antibodies 28 are coupled with biotin molecules 42 and thus selectively bound to endothelial antigens 26 along the endothelial layer. FIG. 3B illustrates avidin molecules 44 coupled to PDT photosensitive drug molecules 30, where the avidin molecules bind with biotin molecules 42. This system thus ensures that the PDT photosensitive drug molecules 30 only bind with the selectively targeted endothelial tissue. When light of the appropriate waveband is administered, it activates the PDT photosensitive drug molecules, causing the endothelial tissue to be destroyed.

FIGS. 4A–4C illustrate a mechanism for amplifying the effect on a tumor of PDT administered to destroy the endothelial tissue in a tumor blood vessel 50. Tumor blood vessel 50 distally branches into two smaller blood vessels 52. In FIG. 4A, the PDT administered to activate the PDT photosensitive drug molecules has produced substantial damage to the endothelium, creating an intravascular thrombosis (or clot) 54. As shown in FIG. 4B, the intravascular thrombosis is carried distally through tumor blood vessel 50 until it reaches the bifurcation point where smaller diameter blood vessels 52 branch. Due to the flow through smaller internal diameter of blood vessels 52, intravascular thrombosis 54 can not advance any further, and is stopped, creating a plug that virtually stops blood flow through tumor blood vessel 50. The interruption of blood flow also interrupts the provision of nutrients and oxygen to the surrounding tumor cells, causing the tumor cells to die. In FIG. 4C, the dying tumor cells are within a zone of necrosis 58 that increases in volume over time, thereby amplifying the effects of the PDT on the endothelium tissue of the tumor blood vessels.

A photosensitizing agent can be administered in a dry formulation, such as pills, capsules, suppositories or patches. The photosensitizing agent also may be administered in a liquid formulation, either alone, with water, or with pharmaceutically acceptable excipients, such as are disclosed in Remington's Pharmaceutical Sciences. The liquid formulation also can be a suspension or an emulsion. In particular, liposomal or lipophilic formulations are desirable. If suspensions or emulsions are utilized, suitable excipients include water, saline, dextrose, glycerol, and the like. These compositions may contain minor amounts of nontoxic auxiliary substances such as wetting or emulsifying agents, antioxidants, pH buffering agents, and the like.

The dose of photosensitizing agent will vary with the target tissue, cells, or composition, the optimal blood level (see Example 1), the animal's weight, and the timing and duration of the radiation administered. Depending on the photosensitizing agent used, an equivalent optimal therapeutic level will have to be empirically established. Preferably, the dose will be calculated to obtain a desired blood level of the photosensitizing agent, which will likely be between about 0.01 $\mu$g/ml and 100 $\mu$g/ml. More preferably, the dose will produce a blood level of the photosensitizing agent between about 0.01 $\mu$g/ml and 10 $\mu$g/ml.

The intensity of radiation used to treat the target cell or target tissue is preferably between about 5 mW/cm$^2$ and about 100 mW/cm$^2$. More preferably, the intensity of radiation employed should be between about 10 mW/cm$^2$ and about 75 mW/cm$^2$. Most preferably, the intensity of radiation is between about 15 mW/cm$^2$ and about 50 mW/cm$^2$.

The duration of radiation exposure administered to a subject is preferably between about 30 minutes and about 72 hours. More preferably, the duration of radiation exposure is between about 60 minutes and about 48 hours. Most preferably, the duration of radiation exposure is between about 2 hours and about 24 hours.

It is contemplated that a targeted photosensitizer agent can be substantially and selectively photoactivated in the target cells and target tissues within a therapeutically reasonable period of time and without excess toxicity or collateral damage to non-target normal tissues. Thus, there appears to be a therapeutic window bounded by the targeted photosensitizer agent dosage and the radiation dosage. In view of problems in the prior art related to either extracorporeal treatment of target tissues or use of high intensity laser light irradiation intra-operatively, the present invention offers substantial advantages. In accord with the present invention, targeted transcutaneous PDT will be employed to treat patients injected with a photosensitizer agent and will subject the patients to a relatively low fluence rate, but high total fluence dose of radiation. This approach is an attractive method for treating target tissues that include neoplastic diseased tissue, infectious agents, and other pathological tissues, cells, and compositions.

One aspect of the present invention is drawn to a method for transcutaneous energy activation therapy applied to destroy tumors in a mammalian subject or patient by first administering to the subject a therapeutically effective amount of a first conjugate comprising a first member of a ligand-receptor binding pair conjugated to an antibody or antibody fragment. The antibody or antibody fragment selectively binds to a target tissue antigen. Simultaneously or subsequently, a therapeutically effective amount of a second conjugate comprising a second member of the ligand-receptor binding pair conjugated to an energy-sensitive agent or energy-intensive agent delivery system or prodrug is administered to the patient, wherein the first member binds to the second member of the ligand-receptor binding pair. These steps are followed by irradiating at least a portion of the subject with energy having a wavelength or waveband absorbed by the energy-sensitive agent, or energy-sensitive agent delivery system, or by the product thereof. This radiation energy is preferably provided by an energy source that is external to the subject and is preferably administered at a relatively low fluence rate that results in the activation of the energy-sensitive agent, or energy-sensitive delivery system, or prodrug product.

While one preferred embodiment of the present invention is drawn to the use of light energy for administering PDT to destroy tumors, other forms of energy are within the scope of this invention, as will be understood by those of ordinary skill in the art. Such forms of energy include, but are not limited to: thermal, sonic, ultrasonic, chemical, light, microwave, ionizing (such as x-ray and gamma ray), mechanical, and electrical. For example, sonodynamically induced or activated agents include, but are not limited to: gallium-porphyrin complex (see Yumita et al., *Cancer Letters*, 112:79–86, (1997)), other porphyrin complexes, such as protoporphyrin and hematoporphyrin (see Umemura et al., *Ultrasonics Sonochemistry* 3:S187–S191, (1996); other cancer drugs, such as daunorubicin and adriamycin, used in the presence of ultrasound therapy (see Yumita et al., *Japan J. Hyperthermic Oncology*, 3(2):175–182, (1987)).

FIG. 5 illustrates the use of an external ultrasound transducer head 60 for generating an ultrasonic beam 62 that penetrates through a dermal layer 64 and into a subcutaneous layer 66. The external ultrasound transducer head is brought into contact with dermal layer 64 so that ultrasonic beam 62 is directed toward a relatively deep tumor 68. The ultrasonic beam activates a PDT photosensitive drug that has been administered to the patient and selectively targeted at tumor 68, causing the drug to destroy the tumor.

This invention further preferably employs an energy source, e.g., a light source, that is external to the target tissue. The target tissues may include and may relate to the vasculature or blood vessels that supply blood to tumor tissue or the target tissues may include the tumor tissue antigens, per se. These target tissue antigens will be readily understood by one of ordinary skill in the art to include but to not be limited to: tumor surface antigen, tumor endothelial antigen, non-tumor endothelial antigen, and tumor vessel wall antigen, or other antigens of blood vessels that supply blood to the tumor.

Where the target tissue includes endothelial or vascular tissue, a preferable ligand-receptor binding pair includes biotin-streptavidin. In this preferred embodiment, the activation of photosensitizer agents by a relatively low fluence rate of a light source over a prolonged period of time results in the direct or indirect destruction, impairment or occlusion of blood supply to the tumor resulting in hypoxia or anoxia to the tumor tissues. Where the target tissue includes tumor tissue other than endothelial or vascular, the activation of photosensitizer agents by a relatively low fluence rate of a light source over a prolonged period of time results in the direct destruction of the tumor tissue due to deprivation of oxygen and nutrients from the tumor cells.

The ordinary skilled artisan would be familiar with various ligand-receptor binding pairs, including those known and those currently yet to be discovered. Those known include, but are not limited to: biotin-streptavidin, chemokine-chemokine receptor, growth factor-growth factor receptor, and antigen-antibody. The present invention contemplates at least one preferred embodiment that uses biotin-streptavidin as the ligand-receptor binding pair. However, the ordinary skilled artisan will readily understand from the present disclosure that any ligand-receptor binding pair may be useful in practicing this invention, provided that the ligand-receptor binding pair demonstrates a specificity for the binding by the ligand to the receptor and further provided that the ligand-receptor binding pair permits the creation of a first conjugate comprising a first member of the ligand-receptor binding pair conjugated to an antibody or antibody fragment. In this case, the antibody or antibody fragment selectively binds to a target tissue antigen and permits the creation of a second conjugate comprising a second member of the ligand-receptor binding pair conjugated to an energy-sensitive or photosensitizing agent, or energy-sensitive or photosensitizing agent delivery system, or prodrug. The first member then binds to the second member of the ligand-receptor binding pair.

Another preferred embodiment of the present invention includes a photosensitizing agent delivery system that utilizes both a liposome delivery system and a photosensitizing agent, where each is separately conjugated to a second member of the ligand-receptor binding pair, and where the first member binds to the second member of the ligand-receptor binding pair. More preferably, the ligand-receptor binding pair is biotin-streptavidin. In this embodiment, the photosensitizing agent as well as the photosensitizing agent delivery system may both be specifically targeted through selective binding to a target tissue antigen by the antibody or antibody fragment of the first member binding pair. Such dual targeting is expected to enhance the specificity of uptake and to increase the quantity of uptake of the photosensitizing agent by the target tissue, cell, or compositions.

EXAMPLES

Having now generally described the invention, it will be more readily understood through reference to the following examples, which are provided by way of illustration and are not intended to be limiting in regard to the scope of the invention, unless specified.

EXAMPLE 1

Transcutaneous Photodynamic Therapy of a Solid Type Tumor

A patient in the terminal phase of recurrent malignant colon cancer presented with a protruding colon carcinoma tumor mass of approximately 500 grams and approximately 13 cm in diameter, which extended through the patient's dermis. Due to the advanced state of the patient's disease and due to the highly vascularized nature of this tumor mass, resection was not feasible. Further, this large tumor mass presented a significant amount of pain and discomfort to the patient, as well as greatly impairing the patient's ability to lie flat.

Six separate light source probes, each including a linear array of LEDs, were surgically implanted in this large human tumor using standard surgical procedures. An intensity of about 25–30 mW of light from each light source probe (650 nm peak wavelength) was delivered to the tumor for 40 hours following oral administration to the patient of a single dose of an (ALA) photosensitizer agent (60 mg/kg). However, after 18 hours, two of the light source probes became unseated from the tumor mass and were disconnected from the electrical power supply used to energize the LEDs on each probe. The total fluence delivered to the tumor bed during this single extended duration treatment was in excess of 20,000 Joules. Extensive tumor necrosis in a radius of up to 5 cm around each of the light source probes was observed after 40 hours of PDT, with no collateral damage to surrounding normal tissue. The extent of this PDT induced necrotic effect in a large volume of tumor tissue was totally unexpected and has not been described before in any PDT studies in subjects in vivo or clinically. Over the course of four weeks following PDT, the necrotic tumor tissue was debrided from the patient resulting in a reduction of approximately 500 grams of tumor tissue. The patient noted a significant improvement in his quality of life, with a resurgent level of energy and improved well being.

The average thickness of human skin is approximately 1 cm. Therefore, if this same method of prolonged, relatively low fluence rate, but overall high total fluence of light delivery is utilized to deliver the light transcutaneously, a therapeutic effect well below the skin surface, to a depth of is contemplated.

The fluence rate employed in this Example represented about 150–180 mW/cm$^2$, with a total fluence more than 20,000 Joules. The preferable fluence rate contemplated more broadly by the present invention is between about 5 mW/cm$^2$ and about 100 mW/cm$^2$, more preferably, between about 10 mW/cm$^2$ and about 75 mW/cm$^2$, and most preferably, between about 15 mW/cm$^2$ and about 50 mW/cm$^2$.

It is further contemplated that the optimal total fluence be empirically determined, using a light dose escalation trial, and will likely and preferably be in the range of about 30 Joules to about 25,000 Joules, and more preferably be in the range from about 100 Joules to about 20,000 Joules, and most preferably be in the range from about 500 Joules to about 10,000 Joules.

EXAMPLE 2

Transcutaneous Photodynamic Therapy of Intraosseous Disease

The current accepted therapy for treating leukemia and other malignant bone marrow diseases employs a systemic treatment utilizing chemotherapy and/or radiotherapy, sometimes followed by a bone marrow transplant. There are significant risks associated with non-discriminative ablative therapies that destroy all marrow elements, including the risks of infections, bleeding diathesis, and other hematological problems.

There is a definite need for alternative therapies that do not subject patients to procedures which may be risky and which inherently cause pain and suffering. This example is directed to a method of treating intraosseous malignancy that has major advantages over the prior art techniques for treating this disease.

A targeted antibody-photosensitizer conjugate (APC) is constructed, which binds selectively to antigens present on leukemic cells. This ligand-receptor binding pair or APC is infused intravenously and is taken up in the marrow by circulating leukemic cells, and by stationary deposits that may reside in other organs. When unbound to leukemic cells, APC is eliminated from the body. Internal or external light sources may be used to activate the targeted drug. For example, light bar probes disclosed in U.S. Pat. No. 5,445,608 may be inserted into bone marrow to treat the intraosseous disease. The devices disclosed in U.S. Pat. No. 5,702,432 may be used to treat disease cells circulating in the patient's lymphatic or vascular system. An external device transcutaneously activating the targeted drug, for example, a light source that emits light that is transmitted through the dermal layer may also be used in treating the marrow compartment in accord with the present invention.

PDT targeting has been described for leukemic cells (see U.S. Pat. No. 5,736,563). but not with capability of treating marrow in situ. Without this capability, simply lowering the leukemic cell count would have little clinical benefit, since the marrow is a major source of new leukemic clones, and the marrow must be protected from failure, which will lead to the death of the patient regardless of how well the pathologic cell load in the circulation is treated. Specific APC promotes the selective damage of leukemic cells in marrow, while reducing collateral and non-target tissue damage. Further, the use of a relatively low fluence rate, but overall high total fluence dose is particularly effective in this therapy. Optimal fluence rates and dosing times are readily empirically determined using dose escalation for both drug and light dose as is often done in a clinical trial. Any of a number of different types of leukemia cell antigens may be selected, provided that the antigen chosen is as specific as possible for the leukemia cell. Such antigens will be known to those of ordinary skill in this art. The selection of a specific photosensitizer agent may be made, provided that the photosensitizer agent chosen is activated by light having a waveband of from about 500 nm to about 1100 nm, and more preferably, a waveband from about 630 nm to about 1000 nm, and most preferably, a waveband from about 800 nm to about 950 nm or greater. The photosensitizer agents noted above are suitable for use in this Example.

With reference to FIG. 6, external light source 10 is administering light 12 transcutaneously through dermal layer 18. Light 12 has a sufficiently long wavelength to pass through a subcutaneous layer 70 and through a cortical bone surface 74, into a bone marrow compartment 76. Leukemia cells 78 have penetrated bone marrow compartment 76 and are distributed about within it. To provide targeted PDT treatment that will destroy the leukemia cells, antibodies 82 bound with PDT photosensitive drug molecules 84 have been administered to the patient and have coupled with leukemia antigens 80 on the leukemia cells. The light provided by external light source 10 thus activates the PDT photosensitive drug, causing it to destroy the leukemia cells. This targeted PDT process is carried out with minimal invasive or adverse impact on the patient, in contrast to the more conventional treatment paradigms currently used.

EXAMPLE 3

Transcutaneous Photodynamic Therapy of Crohn's Disease

Crohn's disease is a chronic inflammation of the gastrointestinal tract thought to be mediated in large part by dysfunction of $CD4^+$ T cells lining the gut mucosa, especially in the terminal ileum. The current accepted therapy for Crohn's disease provides for surgical removal of the inflamed bowel segment and the use of anti-inflammatory agents, steroids and other immunosuppressive drugs. None of these measures is entirely satisfactory due to surgical risk, recurrence of disease, medication side effects, and refractoriness of the disease. There is a clear need for alternative therapies useful in treating this immune dysfunction that offer greater efficacy and reduced side effects and risk. This Example, details of which are illustrated in FIG. 7, indicates the drug compositions and methodologies useful in accord with the present invention to selectively destroy the dysfunctional cells or inhibit their function. In the illustrated example, external light source 10 is administering light 12 that has a sufficiently long wavelength to penetrate dermal tissue 18, which is disposed over a patient's abdomen, and pass through a subcutaneous layer 90, into a terminal ileum or colon 92. The light passes through wall 94 of the terminal ileum or colon. Alternatively (or in addition), light 12' can be administered from an intraluminal probe 96, from sources (not separately shown) that are energized with an electrical current supplied through a lead 98.

Ligand-receptor binding pairs 100, or more specifically, APCs, are created that bind selectively to $CD4^+$ T cell antigens 102 of T cells 104, which are disposed along the interior, intraluminal surface of the terminal ileum or colon. For example, the $CD4^+$ antigen itself may be targeted by those antibodies 106 that bind specifically to the $CD4^+$ antigen. Many of the photosensitizer agents noted above may be used for photosensitizing drug molecules 108, in the therapy of this Example. The APC is preferably formulated into a pharmaceutically acceptable compound that can be released in the terminal ileum and colon in a manner similar to that known to be used for the orally delivered form of Budesonide™ also known as Entocort™. The APC compound is ingested and releases the conjugate into the terminal ileum and colon. At the time of therapy, the bowel should have been prepped in much the same manner as done in preparing for a colonoscopy, so that it is cleared of fecal material. The targeted photosensitizer will bind to the pathologic T cells and any unbound APC is removed via peristaltic action. The sensitizer bound to the T cells is activated by intraluminally positioned light source probe 96, details of which are disclosed in any one of U.S. Pat. Nos.: 5,766,234; 5,782,896; 5,800,478; and 5,827,186, each of which is hereby incorporated by reference herein in its entirety; or by a flexible intraluminal optical fiber (not shown) that is passed via the nasopharynx; or, by the transcutaneous light illumination provided by external light source 10. Transcutaneous light illumination is preferred because it is entirely noninvasive.

In this exemplary treatment, the following protocol may be utilized:

Step 1 Patient is NPO ("non per os" or nothing by mouth) and the bowel has been prepped or cleansed by administering an enema to clear it of fecal material;

Step 2 Specially formulated APC conjugate compound 100 is ingested;

Step 3 The APC conjugate is released to the terminal ileum and colon;

Step 4 If transcutaneous illumination is not used, one or more light source probes 96 are ingested or passed into the GI tract and advanced to the terminal ileum or colon.

Step 5 the APC conjugate is bound to target T cells 104 and any unbound conjugate fraction passes distally via peristalsis (and is subsequently eliminated from the body).

Step 6 If an internal light source is used, the light source should preferably be imaged using ultrasound or computer assisted topography (i.e., a CT scan—not shown) to confirm its location and the light source can then be activated while positioned in the ileum. Once activated, the light source will deliver light at the appropriate waveband for the photosensitizing agent selected, at a relatively low fluence rate, but at a high total fluence dose, as noted above. The optimal drug dose and fluence parameters will be determined clinically in a drug and light dose escalation trial. The light dose and drug dose are such that T cell inactivation occurs, leading to decreased regulation of the immune process and a reduction of any pathologic inflammation both of which are factors characteristic of this disease.

Step 7 The light source is deactivated. It is particularly important to deactivate an internal light source before withdrawing it from the treatment site to prevent nonspecific APC activation.

The present invention can also be employed to target other types of immunologic cells, such as other T cells, macrophages, neutrophils, B cells, and monocytes. A tiered approach can thus be employed, starting with CD4+ T cells, then moving to CD8+ T cells, and then monocytes, and neutrophils. By inhibiting or preventing interaction and/or secretion of inflammatory cell products, the pathologic process is controlled at the lumenal site, completely avoiding systemic side effects and major surgery. The same process can be applied to treat ulcerative colitis with the same benefits. As indicated above, the APC can be activated with light administered transcutaneously, using any number of different types of external light sources such as LEDs, laser diodes, and lamps that emit light with a wavelength or waveband sufficiently long to penetrate through the overlying dermal and internal tissue, and into the intestine. The optimal wavelength or waveband of this light is determined by both the light absorption properties of the photosensitizer and the need to use light with as long a wavelength as possible to ensure adequate penetration into the patient's body. A desirable photosensitizer is preferably one that absorbs in the range from about 700 nm to about 900 nm, which optimizes tissue penetration. The appropriate fluence rate and total fluence delivered is readily determined by a light dose escalation clinical trial. The light dose and drug dose are such that T cell inactivation occurs, leading to reduced regulation of the immune process and a reduction in pathologic inflammation.

EXAMPLE 4

Intraluminal/Transcutaneous PDT Targeted at *Helicobacter pylori*

Targeting of photosensitizers to bind with bacterial cells is known in the prior art. Many antigens that can serve as targets for ligand-receptor binding pairs, and more specifically, APC, have been identified, and the techniques to construct such conjugates are well known to those of ordinary skill in this art. What is not apparent from the prior art are the steps necessary to for apply such conjugates in the treatment of a clinical disease. This Example describes the clinical application of APC to the treatment of an infection using PDT. FIG. 8 illustrates details of the example, as described below.

*Helicobacter pylori* is reportedly associated with tumors of the stomach in mice and as a putative agent of ulcerative pathology in humans. However, it appears that the use of PDT for destroying an *H. pylori* infection in human patients has not been carried out, although proposals to use laser light for PDT destruction of bacteria have been set forth (Millson et al., *J. of Photochemistry and Photobiology*, 32:59–65 (1996)).

In this Example, a capsular or pill-shaped and sized light source 120 is administered orally to a patient, so that it passes into the stomach of the patient, where it administers light 122. Alternatively, an optical fiber (not shown) may be passed into the stomach via the nasopharynx to administer light 122 to the treatment site. In order to implement targeted PDT for treating ulcers in humans, an APC 124, which is targeted against a suitable *Helicobacter pylori* antigen 126 is formulated into an ingestible compound that releases the APC to a gastric mucus/epithelial layer 128 where the bacterium is found. The APC is ingested at a time when the stomach and duodenum is substantially empty in order to promote binding of the APC to bacterium 130. Any unbound APC is diluted by gastric juice and carried distally by peristalsis to be eliminated from the body in fecal matter. Light sources suitable for intraluminal passage are disclosed in any one of U.S. Pat. Nos.: 5,766,234; 5,782,896; 5,800,478; and 5,827,186, the disclosure of each being specifically hereby incorporated herein in its entirety. Alternatively, light source 120 in capsule or pill form, e.g., as disclosed in copending commonly assigned U.S. patent application Ser. No. 09/260,923 entitled, "Polymer Battery for Internal Light Device," filed on Mar. 2, 1999 and which is hereby incorporated in its entirety by reference herein, is used for activating the APC. The light source is preferably energized just prior to its ingestion or remotely after ingestion, when in the stomach or in a desired intraluminal passage. If necessary, multiple light source(s) are ingested to insure that adequate photoactivation of the localized APC occurs sufficient to kill the bacterium. Light is delivered at a relatively low fluence rate but at a high total fluence dose, as discussed above. The light source(s) may be deactivated after passage beyond the duodenum to avoid unwanted distal photoactivation. In this manner, a photosensitizing agent 132 comprising the APC is activated topically without the need for a procedure such as endoscopy with fiber optic gastric illumination in order to provide the activating light. Since the APC is targeted, nonspecific uptake by normal tissue and other normal compositions of the body is minimized in order to prevent injury to normal gastric tissue and problems with the gastric system.

In this exemplary treatment, the following protocol may be utilized:

Step 1 Patient is NPO for six hours to insure that the stomach is empty.

Step 2 The APC is ingested.

Step 3 One hour elapses to allow for bacterial binding and distal passage of unbound APC. The optimal period can be longer or shorter and is readily determined by measuring the clinical response; for example, response can be determined endoscopically by observation and biopsy.

Step 4 One or more light sources are ingested sequentially and activated in the stomach. The length of time that light is administered by these sources and the number of sources that are ingested will be determined clinically in a light dose escalation study. The churning action of the stomach serves to translocate the light source(s) so that the light is distributed more evenly prior to passage of the source(s) into the duodenum. Since each light source is small (the size of a pill or tablet), it passes easily out through the GI system via peristalsis.

Step 5 The light sources are deactivated after distal passage beyond the gastroduodenal area and excreted in fecal matter.

Note that it is also contemplated that an external light source located over the gastric area can be used to transcutaneously administer light to the treatment site, and that an ultrasonic transducer (not shown here, but generally like that shown in FIG. 5) can alternatively be employed to activate the APC, provided that photosensitizer agent 132 comprising the APC is activated by the frequency of ultrasonic energy transmitted by the transducer. The use of an external light source requires that the APC and the light source absorb and emit in the near infrared to infrared range, respectively, so that the light will efficiently penetrate the patient's skin and reach the treatment site. Examples of long waveband photosensitizers are ICG, toluidine blue, and methylene blue, as disclosed herein.

EXAMPLE 5

Transcutaneous PDT for Targeting Pulmonary Tuberculosis

An APC is formulated to bind with great affinity to *Mycobacterium tuberculosis* in a selective and specific manner. Preferably, the APC is formulated as an aerosol, which can be easily inhaled, enabling distribution into all lung segments. Steam is then inhaled to solubilize any unbound APC and facilitate its removal from the lung by exhalation. Alternatively, the APC is formulated as an injectable compound and administered intravenously. Either way, the bound APC is photoactivated by an external light source disposed on the chest and/or back.

Step 1 The APC is inhaled or injected.

Step 2 Time is allowed to elapse to allow binding of the APC with the *Mycobacterium tuberculosis*, followed by steam inhalation to remove any unbound APC (if inhaled). The time required to ensure a therapeutically effective dose of bound APC may be routinely determined clinically using standard clinical practices and procedures.

Step 3 The light source is disposed adjacent to the thorax and activated for a sufficient time to ensure that therapeutic irradiation has occurred, which may be routinely determined clinically using conventional clinical practices and procedures. The fluence rate and total fluence dose may be determined as noted above.

Note that alternatively, an internal light source disposed within the thoracic area can be used to administer the light. A further alternative would be the use of an external ultrasonic transducer to produce ultrasonic sound waves that activate the APC. The use of an external light source requires that the APC and the light source respectively absorb and emit light in the near infrared to infrared range to ensure efficient skin penetration of the light. Examples of long waveband photosensitizers are ICG, toluidine blue, methylene blue.

EXAMPLE 6

Transcutaneous PDT for Targeting Otitis Media

A photosensitizer conjugate is formulated which binds with great affinity to *Streptococcus pneumoniae* and *Hemophilus influenzae* in a selective manner. The APC is formulated into an injectable compound, which can be administered intravenously or instilled topically into the middle ear via a previously placed tympanostomy tube. The drug is activated using light emitted by a small light source about the size, shape, and weight of a hearing aid, which is disposed behind the ear and aimed at the middle ear, so that the light passes into the middle ear transcutaneously.

Step 1 the APC fluid formulation is instilled into the middle ear.

Step 2 Sufficient time is allowed to elapse to allow binding of the APC with the disease organisms, and then, any excess fluid is drained away by gravity or actively aspirated using a needle and syringe.

Step 3 The light source is positioned behind the ear and activated. The light source need not be very intense since the middle ear cavity is small. Further, the fluence rate and total fluence dose may be followed as discussed above.

EXAMPLE 7

Transcutaneous PDT for Targeting Antibiotic Associated Pseudomembranous Colitis In cases where *Clostridium difficile* causes pseudomembranous colitis, the same scheme disclosed above for the treatment of *H. pylori* may be applied. The difference is that the APC is targeted toward *C. difficile* and the ingested light source is activated in the colon rather than in the stomach. Alternatively, the photosensitive agent can be activated with transcutaneously transmitted light from an external light source, or by ultrasonic energy produced by an ultrasonic transmitter.

EXAMPLE 8

Transcutaneous PDT for Targeting Septic Shock Disease

A number of anti-endotoxin antibodies and peptides have been developed and synthesized that can be bound to photosensitizers to form anti-endotoxin APCs. These APCs are injected, allowed to bind and then activated transcutaneously with light, or by using the intracorporeal light emitting devices disclosed in U.S. Pat. No. 5,702,432. For transcutaneous activation, an external light source is placed over a major vessel, preferably an artery, but most preferably a vein where the blood flow is slower, to allow more time for APC activation.

EXAMPLE 9

Liver Cancer Photodynamic Therapy by Transillumination

This Example uses the present invention for the treatment of an organ infiltrated with tumor tissue. Reference is made to FIG. 9. Specifically, light 140 is administered by transillumination through liver tissue 142 from an implanted light source 144 that is disposed external to the surface of liver 142, but within the patient's body. In this embodiment, a patient is injected intravenously with a photosensitizer agent ICG, conjugated to an antibody that is specific to vascular endothelial antigen (not separately shown) on a tumor 146, so that the antibody binds with the antigen, but not to other tissue in the liver. The optimal dose of ICG will be empirically determined, for example, via a dose escalation clinical trial as is so often performed to evaluate chemotherapeutic agents. One or more light source probes 144 are surgically implanted (e.g., endoscopically) adjacent to, but not invading parenchymal tissue 148 of liver 142. After delaying a time sufficient to permit clearing of the photosensitizer conjugate from the non-target tissues, the light source(s) is(are) activated, irradiating the target tissue with light 140 at a relatively low fluence rate, but administering a high total fluence dose of light in the waveband from about 750 nm to about 850 nm.

The specific dose of photosensitizer conjugate administered to the patient is that which will result in a concentration of active ICG in the blood of between about 0.01 µg/ml and about 100 µg/ml and more preferably, between about 0.01 µg/ml and about 10 µg/ml. It is well within the skill of the ordinary skilled artisan to determine the specific therapeutically effective dose using standard clinical practices and procedures. Similarly, a specific acceptable fluence rate and a total fluence dose may be empirically determined based upon the information provided in this disclosure.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for administering a photodynamic therapy to a target tissue or composition in a mammalian subject, comprising the steps of:
    (a) administering to the subject a therapeutically effective amount of a targeted photoreactive compound having a characteristic light absorption waveband, said targeted photoreactive compound selectively binding with the target tissue or composition, but not binding with a non-target tissue or composition;
    (b) transdermally irradiating at least a portion of the mammalian subject in which the target tissue or composition to which the targeted photoreactive compound has bound is disposed, with light having a waveband corresponding at least in part to the characteristic light absorption waveband of said targeted photoreactive compound; wherein
        the intensity of the light used for the step of transdermally irradiating and the duration of irradiation have been selected such that the target tissue or composition is destroyed and the non-target tissue or composition through which the light passes remains undamaged.

2. The method of claim 1, further comprising the step of allowing sufficient time for any targeted photoreactive compound that is not bound to the target tissue or composition to clear from the non-target tissue or composition of the mammalian subject prior to the step of irradiating.

3. The method of claim 1, wherein said target tissue is vascular endothelial tissue.

4. The method of claim 1, wherein said target tissue is an abnormal vascular wall of a tumor.

5. The method of claim 1, wherein the target tissue or composition is selected from the group consisting of: a vascular endothelial tissue, an abnormal vascular wall of a tumor, a solid tumor, a tumor of a head, a tumor of a neck, a tumor of a gastrointestinal tract, a tumor of a liver, a tumor of a breast, a tumor of a prostate, a tumors of a lung, a nonsolid tumor, malignant cells of one of a hematopoietic tissue and a lymphoid tissue, lesions in a vascular system, a diseased bone marrow, and diseased cells in which the disease is one of an autoimmune and an inflammatory disease.

6. The method of claim 1, wherein said target tissue is a lesion in a vascular system.

7. The method of claim 1, wherein the step of irradiating comprises the step of providing a light source that is disposed external to an intact skin layer of the mammalian subject and wherein said light source is activated to produce the light.

8. The method of claim 1, wherein the photosensitizer compound comprises one of:
    (a) a targeted photosensitizing agent;
    (b) a photosensitizing agent delivery system that delivers the targeted photosensitizing agent to bind with the target tissue; and
    (c) a prodrug that produces a prodrug product, said prodrug product selectively binding to the target tissue.

9. The method of claim 8, wherein said photosensitizing agent is conjugated to a ligand.

10. The method of claim 9, wherein said ligand is one of an antibody and an antibody fragment that is specific in binding with the target tissue.

11. The method of claim 9, wherein said ligand is a peptide that is specific in binding with the target tissue.

12. The method of claim 1, wherein said photosensitizer compound is selected from the group consisting of indocyanine green, methylene blue, toluidine blue, aminolevulinic acid, chlorins, phthalocyanines, porphyrins, purpurins, and texaphyrins.

13. The method of claim 1, wherein the step of irradiating is carried out for a time interval of from about 30 minutes to about 72 hours.

14. The method of claim 1, wherein the step of irradiating is carried out for a time interval of from about 60 minutes to about 48 hours.

15. The method of claim 1, wherein the step of irradiating is carried out for a time interval of from about 3 hours to about 24 hours.

16. The method of claim 1, wherein the target tissue or composition is a lesion of a type selected from the group consisting of atherosclerotic lesions, arteriovenous malformations, aneurysms, and venous lesions.

17. The method of claim 1, wherein the intensity of the light used for the step of transdermally irradiating is substantially less than 500 mw/cm$^2$.

18. The method of claim 1, wherein the intensity of the light used for the step of transdermally irradiating is between about 5 mW/cm$^2$ and about 100 mW/cm$^2$.

19. The method of claim 1, wherein the intensity of the light used for the step of transdermally irradiating is between about 10 mW/cm$^2$ and about 75 mW/cm$^2$.

20. The method of claim 1, wherein the intensity of the light used for the step of transdermally irradiating is between about 15 mW/cm$^2$ and about 50 mW/cm$^2$.

21. The method of claim 1, wherein the targeted photoreactive compound is conjugated to a ligand comprising a polymer that is specific in binding with the target tissue or composition.

22. A method for administering a photodynamic therapy to a target tissue or composition in a mammalian subject, comprising the steps of:
(a) administering to the mammalian subject a therapeutically effective amount of a first conjugate comprising a first member of a ligand-receptor binding pair conjugated to one of an antibody and an antibody fragment, wherein said one of the antibody and the antibody fragment selectively binds to an antigen of the target tissue or composition;
(b) administering to the mammalian subject a therapeutically effective amount of a second conjugate comprising a second member of the ligand-receptor binding pair, conjugated to a photoreactive compound; and
(c) transdermally irradiating at least a portion of the mammalian subject in which the target tissue or composition that has bound to said one of the antibody and the antibody fragment is disposed, using light having a waveband corresponding at least in part to the characteristic light absorption waveband of said photoreactive compound; wherein
the intensity of the light used for the step of transdermally irradiating and the duration of irradiation have been selected such that the target tissue or composition is destroyed and the non-target tissue or composition through which the light passes remains undamaged.

23. The method of claim 22, wherein said target tissue is one of a vascular endothelial tissue and an abnormal vascular wall of a tumor.

24. The method of claim 22, wherein the target tissue is a tumor disposed in one of a head, a neck, a gastrointestinal tract, a liver, a breast, a prostate, and a lung.

25. The method of claim 22, wherein the target tissue is selected from the group consisting of: a nonsolid tumor; malignant cells in hematopoietic tissue; malignant cells in lymphoid tissue; lesions in a vascular system; a diseased bone marrow; cells afflicted with an autoimmune disease; and cells afflicted with an inflammatory disease.

26. The method of claim 22, wherein the ligand-receptor binding pair is selected from the group consisting of a biotin-streptavidin, a chemokine-chemokine receptor, a growth factor-growth factor receptor, and an antigen-antibody.

27. The method of claim 22, wherein the targeted photoreactive compound comprises one of:
(a) a targeted photosensitizing agent;
(b) a photosensitizing agent delivery system that delivers the targeted photosensitizing agent to bind with the target tissue; and
(c) a prodrug that produces a prodrug product, said prodrug product selectively binding to the target tissue.

28. The method of claim 27, wherein said photosensitizing agent delivery system includes a photosensitizing agent conjugated with a targeted liposome.

29. The method of claim 22, wherein the intensity of the light used for the step of transdermally irradiating is substantially less than 500 mw/cm$^2$.

30. A method for transcutaneously administering a photodynamic therapy to a target tissue in a mammalian subject, wherein said target tissue is bone marrow, comprising the steps of:
(a) administering to the subject a therapeutically effective amount of a targeted photoreactive compound having a characteristic light absorption waveband, said targeted photoreactive compound selectively binding with the target tissue, but not binding with non-target tissue;
(b) transcutaneously irradiating at least a portion of the mammalian subject in which the target tissue to which the targeted photoreactive compound has bound is disposed, with light having a waveband corresponding at least in part to the characteristic light absorption waveband of said targeted photoreactive compound; and
(c) ensuring that an intensity of the light used for the step of transcutaneously irradiating is substantially less than 500 mw/cm$^2$, and that a total fluence of the light used for irradiating is sufficiently high to activate said targeted photoreactive compound, said light-activating the targeted photoreactive compound, causing said target tissue to be destroyed.

31. A method for transcutaneously administering a photodynamic therapy to a target tissue in a mammalian subject, wherein said target tissue comprises diseased cells in which the disease is one of an autoimmune and an inflammatory disease, comprising the steps of:
(a) administering to the subject a therapeutically effective amount of a targeted photoreactive compound having a characteristic light absorption waveband, said targeted photoreactive compound selectively binding with the target tissue, but not binding with non-target tissue;
(b) transcutaneously irradiating at least a portion of the mammalian subject in which the target tissue to which the targeted photoreactive compound has bound is disposed, with light having a waveband corresponding at least in part to the characteristic light absorption waveband of said targeted photoreactive compound; and
(c) ensuring that an intensity of the light used for the step of transcutaneously irradiating is substantially than 500 mw/cm$^2$, and that a total fluence of the light used for irradiating is sufficiently high to activate said targeted photoreactive compound, said light activating the targeted photoreactive compound, causing said target tissue to be destroyed.

32. A method for administering a photodynamic therapy to a target tissue or composition in a mammalian subject, said method comprising:
a) administering to the subject a therapeutically effective amount of a targeted photoreactive compound which preferentially associates with the target tissue or composition and not with a non-target tissue or composition, wherein said target tissue or composition is located greater than 2 centimeters below the surface of the skin; and
b) transdermally irradiating at least a portion of the subject with light, whereby the targeted photoreactive compound is activated and the target tissue or composition is destroyed.

33. The method of claim 32, wherein the intensity of the light used for the step of transdermally irradiating and the duration of irradiation have been selected such that the target tissue or composition is destroyed and the non-target tissue or composition through which the light passes remains undamaged.

34. The method of claim 32, wherein, the intensity of the light used for the step of transdermally irradiating is substantially less than 500 mW/cm$^2$, and the total fluence of the light used for irradiating is sufficiently high to activate said targeted photoreactive compound.

35. The method of claim 32, wherein the intensity of the light used for the step of transdermally irradiating is between about 5 mW/cm$^2$ and about 100 mW/cm$^2$, and the total fluence of the light used for irradiating is sufficiently high to activate said targeted photoreactive compound.

36. The method of claim 32, wherein the intensity of the light used for the step of transdermally irradiating is between about 10 mW/cm$^2$ and about 75 mW/cm$^2$, and the total fluence of the light used for irradiating is sufficiently high to activate said targeted photoreactive compound.

37. The method of claim 32, wherein the intensity of the light used for the step of transdermally irradiating is between about 15 mW/cm$^2$ and about 50 mW/cm$^2$, and the total fluence of the light used for irradiating is sufficiently high to activate said targeted photoreactive compound.

* * * * *

UNITED STATES PATENT AND TRADEMARK OFFICE
CERTIFICATE OF CORRECTION

PATENT NO. : 6,602,274 B1
DATED : August 5, 2003
INVENTOR(S) : James Chen

It is certified that error appears in the above-identified patent and that said Letters Patent is hereby corrected as shown below:

Column 18,
Lines 37-42, please replace "copending commonly assigned U.S. Patent application Ser. No. 09/260,923 entitled, "Polymer Battery for Internal Light Device." filed on March 2, 1999 and which is hereby incorporated in its entirety by reference herein," with —U.S. Patent No. 6,273,904—

Columns 22, 23 and 24,
Replace Claims 8, 12, 17, 27, 29, 30, and 31 with the following Claims:

8. The method of Claim 1, wherein the photoreactive compound comprises one of:
   (a) a targeted photosensitizing agent;
   (b) a photosensitizing agent delivery system that delivers the targeted photosensitizing agent to bind with the target tissue; and
   (c) a prodrug that produces a prodrug product, said prodrug product selectively binding to the target tissue.

12. The method of Claim 1, wherein said photoreactive compound is selected from the group consisting of indocyanine green, methylene blue, toluidine blue, aminolevulinic acid, chlorins, phthalocyanines, porphyrins, purpurins, and texaphyrins.

17. The method of claim 1, wherein the intensity of the light used for the step of transdermally irradiating is substantially less than 500 mW/cm$^2$.

27. The method of Claim 22, wherein the photoreactive compound comprises one of:
   (a) a targeted photosensitizing agent;
   (b) a photosensitizing agent delivery system that delivers the targeted photosensitizing agent to bind with the target tissue; and
   (c) a prodrug that produces a prodrug product, said prodrug product selectively binding to the target tissue.

29. The method of claim 22, wherein the intensity of the light used for the step of transdermally irradiating is substantially less than 500 mW/cm$^2$.

30. A method for transcutaneously administering a photodynamic therapy to a target tissue in a mammalian subject, wherein said target tissue is bone marrow, comprising the steps of:
   (a) administering to the subject a therapeutically effective amount of a targeted photoreactive compound having a characteristic light absorption waveband, said targeted photoreactive compound selectively binding with the target tissue, but not binding with non-target tissue;
   (b) transcutaneously irradiating at least a portion of the mammalian subject in which the target tissue to which the targeted photoreactive compound has bound is disposed, with light having a waveband corresponding at least in part to the characteristic light absorption waveband of said targeted photoreactive compound; and
   (c) ensuring that an intensity of the light used for the step of transcutaneously irradiating is substantially less than 500 mW/cm$^2$, and that a total fluence of the light used for irradiating is sufficiently high to activate said targeted photoreactive compound, said light activating the targeted photoreactive compound, causing said target tissue to be destroyed.

UNITED STATES PATENT AND TRADEMARK OFFICE
CERTIFICATE OF CORRECTION

PATENT NO. : 6,602,274 B1
DATED : August 5, 2003
INVENTOR(S) : James Chen

It is certified that error appears in the above-identified patent and that said Letters Patent is hereby corrected as shown below:

<u>Claims cont'd.</u>,

31. A method for transcutaneously administering a photodynamic therapy to a target tissue in a mammalian subject, wherein said target tissue comprises diseased cells in which the disease is one of an autoimmune and an inflammatory disease, comprising the steps of:
    (a) administering to the subject a therapeutically effective amount of a targeted photoreactive compound having a characteristic light absorption waveband, said targeted photoreactive compound selectively binding with the target tissue, but not binding with non-target tissue;
    (b) transcutaneously irradiating at least a portion of the mammalian subject in which the target tissue to which the targeted photoreactive compound has bound is disposed, with light having a waveband corresponding at least in part to the characteristic light absorption waveband of said targeted photoreactive compound; and
    (c) ensuring that an intensity of the light used for the step of transcutaneously irradiating is substantially less than 500 $mW/cm^2$, and that a total fluence of the light used for irradiating is sufficiently high to activate said targeted photoreactive compound, said light activating the targeted photoreactive compound, causing said target tissue to be destroyed.

Signed and Sealed this

Fourteenth Day of December, 2004

JON W. DUDAS
*Director of the United States Patent and Trademark Office*